(12) United States Patent
Bath et al.

(10) Patent No.: US 11,998,701 B2
(45) Date of Patent: Jun. 4, 2024

(54) APPARATUS FOR TREATING A RESPIRATORY DISORDER IN A PATIENT

(71) Applicant: ResMed Pty Ltd, Bella Vista (AU)

(72) Inventors: Andrew Roderick Bath, Sydney (AU); Justin John Formica, Sydney (AU); Matthew Rolf Harrington, Gosford (AU); Joseph Samuel Ormrod, Sydney (AU); Luke Andrew Stanislas, Sydney (AU); Hargopal Verma, Sydney (AU)

(73) Assignee: ResMed Pty Ltd, Bella Vista (AU)

( * ) Notice: Subject to any disclaimer, the term of this patent is extended or adjusted under 35 U.S.C. 154(b) by 0 days.

(21) Appl. No.: 17/704,188

(22) Filed: Mar. 25, 2022

(65) Prior Publication Data

US 2022/0211969 A1    Jul. 7, 2022

Related U.S. Application Data

(63) Continuation of application No. 17/322,947, filed on May 18, 2021, which is a continuation of application
(Continued)

(30) Foreign Application Priority Data

Mar. 15, 2013   (AU) .............................. 2013900901

(51) Int. Cl.
*A61M 16/00*     (2006.01)
*A61M 16/06*     (2006.01)
(Continued)

(52) U.S. Cl.
CPC .......... *A61M 16/16* (2013.01); *A61M 16/021* (2017.08); *A61M 16/0683* (2013.01);
(Continued)

(58) Field of Classification Search
CPC .............. A61M 16/109; A61M 16/021; A61M 16/0683; A61M 16/0066;
(Continued)

(56) References Cited

U.S. PATENT DOCUMENTS 2,023,324 A    12/1935  Johnson
2,139,429 A    12/1938  Wilson
(Continued)

FOREIGN PATENT DOCUMENTS

AU    2003265025 B2    4/2004
CA    2151992          6/1996
(Continued)

OTHER PUBLICATIONS

Office Action dated Oct. 2, 2017 issued in Taiwanese Application No. 103109227 with English translation (11 pages).
(Continued)

*Primary Examiner* — T. Bennett McKenzie
(74) *Attorney, Agent, or Firm* — Nixon & Vanderhye P.C.

(57) ABSTRACT

An apparatus for treating a respiratory disorder in a patient includes a blower configured to generate a supply of pressurized respiratory air to the patient via an air delivery tube leading to a patient interface; a dock with a heater plate; and a reservoir comprising a conductive portion configured to thermally engage the heater plate.

21 Claims, 35 Drawing Sheets

Related U.S. Application Data

No. 15/825,166, filed on Nov. 29, 2017, now Pat. No. 11,013,881, which is a continuation of application No. 14/211,346, filed on Mar. 14, 2014, now Pat. No. 9,861,778.

(51) Int. Cl.
*A61M 16/10* (2006.01)
*A61M 16/16* (2006.01)

(52) U.S. Cl.
CPC ... *A61M 16/109* (2014.02); *A61M 2016/0039* (2013.01); *A61M 16/0066* (2013.01); *A61M 16/161* (2014.02); *A61M 2205/123* (2013.01); *A61M 2205/3368* (2013.01); *A61M 2205/42* (2013.01)

(58) Field of Classification Search
CPC .. A61M 2016/0039; A61M 2016/0042; A61M 2205/123; A61M 2205/3368; A61M 2205/42; A61M 16/1045; A61M 16/16–161; A61M 16/051
USPC .......................... 392/386–406; 261/127–157
See application file for complete search history.

(56) References Cited

U.S. PATENT DOCUMENTS

| | | |
|---|---|---|
| 3,348,821 A | 10/1967 | Martin |
| 3,414,117 A | 12/1968 | Leeds |
| 3,479,801 A | 11/1969 | Yamasaki |
| 3,617,698 A | 11/1971 | Duncanson |
| 4,098,853 A | 7/1978 | Brown |
| 4,203,027 A * | 5/1980 | O'Hare ................. A61M 16/16 261/142 |
| 4,311,317 A | 1/1982 | Bartels |
| 4,670,144 A | 6/1987 | McCausland |
| 4,782,832 A | 11/1988 | Trimble et al. |
| 4,836,401 A | 6/1989 | Ingemann |
| 4,921,642 A | 5/1990 | Latorraca |
| 4,944,310 A | 7/1990 | Sullivan |
| 4,986,937 A | 1/1991 | Sorio |
| 5,215,685 A | 6/1993 | Marino |
| 5,514,303 A | 5/1996 | Chiu |
| 5,529,060 A | 6/1996 | Salmon et al. |
| 5,564,415 A | 10/1996 | Dobson et al. |
| 5,701,950 A | 12/1997 | Imamura et al. |
| 5,704,345 A | 1/1998 | Berthon-Jones |
| 5,761,030 A * | 6/1998 | Roscoe ................... G06F 1/184 361/801 |
| 5,769,517 A * | 6/1998 | Carde ....................... E05C 3/14 312/334.47 |
| 5,943,473 A | 8/1999 | Levine |
| 5,957,554 A | 9/1999 | Pendergast |
| 6,244,576 B1 | 6/2001 | Tsai |
| 6,256,454 B1 | 7/2001 | Dykes |
| 6,397,841 B1 * | 6/2002 | Kenyon ................ A61M 16/08 128/204.14 |
| 6,398,197 B1 | 6/2002 | Dickinson et al. |
| 6,427,984 B1 | 8/2002 | Mulvaney |
| 6,435,180 B1 | 8/2002 | Hewson |
| 6,532,959 B1 | 3/2003 | Berthon-Jones |
| 6,669,626 B1 * | 12/2003 | McDonough .......... A61G 11/00 600/22 |
| 6,918,389 B2 | 7/2005 | Seakins et al. |
| 7,111,624 B2 | 9/2006 | Thudor et al. |
| 7,261,329 B1 * | 8/2007 | Julian ................. E05B 65/0014 292/87 |
| 7,413,173 B2 | 8/2008 | DiMatteo et al. |
| 7,677,246 B2 | 3/2010 | Kepler et al. |
| 7,866,944 B2 | 1/2011 | Kenyon et al. |
| 8,006,691 B2 | 8/2011 | Kenyon et al. |
| 8,631,789 B2 | 1/2014 | Virr et al. |
| 8,636,479 B2 | 1/2014 | Kenyon et al. |
| 8,638,014 B2 | 1/2014 | Sears et al. |
| 8,739,780 B2 | 6/2014 | Tang et al. |
| 8,770,432 B2 | 7/2014 | Rueckeim |
| 9,227,035 B2 | 1/2016 | Crumblin et al. |
| 9,707,370 B2 | 7/2017 | Smith et al. |
| 10,342,950 B2 | 7/2019 | Bath et al. |
| 2001/0017134 A1 | 8/2001 | Bahr |
| 2001/0050080 A1 | 12/2001 | Seakins et al. |
| 2004/0060559 A1 | 4/2004 | Virr |
| 2004/0234254 A1 * | 11/2004 | Czupich ............. A61M 16/109 392/403 |
| 2005/0185938 A1 * | 8/2005 | Ruiz Ballesteros ........................ A01M 1/2077 392/386 |
| 2006/0055069 A1 | 3/2006 | DiMatteo |
| 2007/0034638 A1 * | 2/2007 | Zeiron ................. A47K 10/427 221/52 |
| 2007/0079826 A1 | 4/2007 | Kramer et al. |
| 2007/0132117 A1 | 6/2007 | Pujol et al. |
| 2007/0169776 A1 * | 7/2007 | Kepler ................ A61M 16/107 128/200.14 |
| 2008/0073802 A1 | 3/2008 | Anderson et al. |
| 2008/0142019 A1 | 6/2008 | Lewis |
| 2008/0251071 A1 | 10/2008 | Armitstead et al. |
| 2008/0302361 A1 | 12/2008 | Snow |
| 2009/0000620 A1 | 1/2009 | Virr |
| 2009/0044808 A1 | 2/2009 | Guney et al. |
| 2009/0050156 A1 | 2/2009 | Ng et al. |
| 2009/0194106 A1 | 8/2009 | Smith et al. |
| 2009/0223514 A1 | 9/2009 | Smith |
| 2010/0000534 A1 | 1/2010 | Kooij et al. |
| 2010/0043791 A1 | 2/2010 | McAuley |
| 2010/0065051 A1 | 3/2010 | Potharaju |
| 2010/0154796 A1 | 6/2010 | Smith |
| 2011/0017212 A1 | 1/2011 | Kenyon |
| 2011/0023674 A1 | 2/2011 | Bath et al. |
| 2011/0155132 A1 | 6/2011 | Virr et al. |
| 2011/0162649 A1 | 7/2011 | Potharaju et al. |
| 2011/0180068 A1 | 7/2011 | Kenyon et al. |
| 2011/0248082 A1 | 10/2011 | Treacy |
| 2012/0074825 A1 | 3/2012 | Armstrong |
| 2012/0097163 A1 | 4/2012 | Potharaju |
| 2012/0248636 A1 | 10/2012 | Fridberg |
| 2012/0279984 A1 * | 11/2012 | Brolin ................. A47K 10/426 221/197 |
| 2013/0008440 A1 | 1/2013 | Maurer et al. |
| 2013/0096490 A1 | 4/2013 | Pelkus |
| 2013/0174843 A1 | 7/2013 | Smith |
| 2014/0264975 A1 | 9/2014 | Bath et al. |
| 2016/0022954 A1 | 1/2016 | Bath et al. |
| 2018/0078730 A1 | 3/2018 | Bath et al. |
| 2021/0268223 A1 | 9/2021 | Bath et al. |

FOREIGN PATENT DOCUMENTS

| | | |
|---|---|---|
| CN | 101537221 A | 9/2009 |
| CN | 101583395 A | 11/2009 |
| CN | 101678190 A | 3/2010 |
| CN | 201954697 U | 8/2011 |
| EP | 2 540 335 A1 | 1/2013 |
| EP | 2 703 034 A2 | 3/2014 |
| GB | 1 401 399 | 7/1975 |
| GB | 1 450 097 | 9/1976 |
| GB | 2 010 097 A | 6/1979 |
| JP | 48-23271 U | 7/1973 |
| JP | 59-55316 U | 4/1984 |
| JP | 5-312363 A | 11/1993 |
| JP | 7-55210 A | 3/1995 |
| JP | 10-76008 A | 3/1998 |
| JP | 2004-188121 | 7/2004 |
| JP | 2005-538802 A | 12/2005 |
| JP | 2009-508647 A | 3/2009 |
| JP | 2010-203626 A | 9/2010 |
| JP | 2012-502698 A | 2/2012 |
| WO | WO 98/04310 | 2/1998 |
| WO | WO 98/04311 A1 | 2/1998 |
| WO | WO 98/34665 | 8/1998 |
| WO | WO 98/57691 A1 | 12/1998 |

(56) References Cited

FOREIGN PATENT DOCUMENTS

| | | |
|---|---|---|
| WO | WO 00/78381 | 12/2000 |
| WO | WO 01/10489 A2 | 2/2001 |
| WO | WO 02/066107 A1 | 8/2002 |
| WO | 2004/026382 | 4/2004 |
| WO | WO 2004/073778 | 9/2004 |
| WO | WO 2004/112873 | 12/2004 |
| WO | WO 2005/063328 | 7/2005 |
| WO | WO 2006/074513 | 7/2006 |
| WO | WO 2006/130903 | 12/2006 |
| WO | WO 2007/019625 | 2/2007 |
| WO | 2007/038152 | 4/2007 |
| WO | WO 2007/045017 A2 | 4/2007 |
| WO | 2008/056993 | 5/2008 |
| WO | 2008/076230 | 6/2008 |
| WO | WO 2009/052560 | 4/2009 |
| WO | WO 2009/156921 | 12/2009 |
| WO | 2010/031126 | 3/2010 |
| WO | WO 2010/135785 | 12/2010 |
| WO | WO 2011/080601 A1 | 7/2011 |
| WO | 2012/171072 A1 | 12/2012 |
| WO | WO 2012/171072 | 12/2012 |
| WO | WO 2013/020167 | 2/2013 |
| WO | 2014/038968 | 3/2014 |

OTHER PUBLICATIONS

Communication dated May 30, 2017 issued in European Application No. 14 763 136.0 (7 pages).
Patent Examination Report No. 2 dated Oct. 19, 2016 issued in Australian Application No. 2014231714 (4 pages).
Extended European Search Report issued in a related European Application No. 14763136.0 dated Sep. 7, 2016.
International Search Report issued in related Application No. PCT/AU2014/000264, dated May 13, 2014, 8 pages.
Written Opinion of the International Searching Authority issued in related Application No. PCT/AU2014/000264, dated May 13, 2014, 4 pages.
"Respiratory Physiology", by John B. West, Lippincott Williams & Wilkins, 9th edition published 2011, 8 pages.
CPAP System XT Series, Apex Medical Corp., published Aug. 2007, 4 pages.
International Preliminary Report on Patentability issued in related PCT/AU2014/000264 dated Sep. 15, 2015.
First Examination Report issued in related New Zealand Application No. 631374 dated Oct. 29, 2015.
Patent Examination Report No. 1 issued in related Australian Application No. 2014231714 dated Mar. 23, 2016.
First Office Action issued in related CN Application No. 201480028533.9 dated Jun. 30, 2016, with English langauge translation thereof.
APEX XT-Auto Instruction Manual, USPTO to assume before Applicant's filing date.
APEX "Introducing a new member of our CPAP family" APEX XT-Auto, USPTO to assume before Applicant's filing date.
Notice of Reasons for Rejection dated Jan. 5, 2018 issued in Japanese Application No. 2015-561828 with English translation (11 pages).
Communication dated Jul. 16, 2018 issued in European Application No. 14763136.0 (8 pages).
Office Action dated Aug. 27, 2018 issued in related U.S. Appl. No. 14/777,266 (38 pages).
Bath et al., U.S. Appl. No. 15/825,166, filed Nov. 29, 2017, entitled "Humidifier Reservoir," (patent application).
P.W. Bridgman, "The Effect of Thermal Conductivity of Metals," Proceedings of the American Academy of Arts and Sciences, vol. 57, No. 5, Apr. 1922, pp. 110-113.
Bath et al., U.S. Appl. No. 17/322,947, filed May 18, 2021, entitled "Humidifier Reservoir," (parent application).
U.S. Appl. No. 17/471,856, filed Sep. 10, 2021, of Bath et al., entitled "Humidifier Reservoir," 218 pages.
U.S. Appl. No. 17/481,860, filed Sep. 22, 2021, of Bath et al., entitled "Humidifier Reservoir," 217 pages.
U.S. Appl. No. 17/509,380, filed Oct. 25, 2021, of Bath et al., entitled "Humidifier Reservoir," 212 pages.
U.S. Appl. No. 17/509,151, filed Oct. 25, 2021, of Bath et al., entitled "Humidifier Reservoir," 271 pages.
U.S. Appl. No. 17/480,286, filed Sep. 21, 2021, of Bath et al., entitled "Humidifier Reservoir," 168 pages.
U.S. Appl. No. 17/481,466, filed Sep. 22, 2021, of Bath et al., entitled "Humidifier Reservoir," 222 pages.
U.S. Appl. No. 17/482,838, filed Sep. 23, 2021, of Bath et al., entitled "Humidifier Reservoir," 249 pages.
U.S. Appl. No. 17/485,625, filed Sep. 27, 2021, of Bath et al., entitled "Humidifier Reservoir," 213 pages.
U.S. Appl. No. 17/505,761, filed Oct. 20, 2021, of Bath et al., entitled "Humidifier Reservoir," 229 pages.
U.S. Appl. No. 17/488,849, filed Sep. 29, 2021, of Bath et al., entitled "Humidifier Reservoir," 155 pages.
U.S. Appl. No. 17/489,000, filed Sep. 29, 2021, of Bath et al., entitled "Humidifier Reservoir," 242 pages.
U.S. Appl. No. 17/508,018, filed Oct. 22, 2021, of Bath et al., entitled "Humidifier Reservoir," 213 pages.
U.S. Appl. No. 17/509,546, filed Oct. 25, 2021, of Bath et al., entitled "Humidifier Reservoir," 220 pages.
U.S. Appl. No. 17/677,449, filed Feb. 22, 2022, of Bath et al., entitled "Medical Treatment Apparatus and Water Reservoir for Same," 129 pages.
Office Action issued in U.S. Appl. No. 18/162,823 dated May 25, 2023, 44 pages.

* cited by examiner

APPARATUS FOR TREATING A RESPIRATORY DISORDER IN A PATIENT

1 CROSS-REFERENCE TO RELATED APPLICATIONS

This application is a continuation of U.S. application Ser. No. 17/322,947, filed May 18, 2021, which is a continuation of U.S. application Ser. No. 15/825,166, filed Nov. 29, 2017, now U.S. Pat. No. 11,013,881, which is a continuation of U.S. application Ser. No. 14/211,346, filed Mar. 14, 2014, now U.S. Pat. No. 9,861,778, which claims the benefit of Australian Provisional Application No. 2013900901, filed Mar. 15, 2013, each of which is incorporated herein by reference in its entirety.

A portion of the disclosure of this patent document contains material which is subject to copyright protection. The copyright owner has no objection to the facsimile reproduction by anyone of the patent document or the patent disclosure, as it appears in Patent Office patent files or records, but otherwise reserves all copyright rights whatsoever.

2 BACKGROUND OF THE INVENTION

2.1 (1) Field of the Invention

The present technology relates to one or more of the diagnosis, treatment and amelioration of respiratory disorders, and to procedures to prevent respiratory disorders. In particular, the present technology relates to medical devices, and their use for treating respiratory disorders and for preventing respiratory disorders.

2.2 (2) Description of the Related Art

The respiratory system of the body facilitates gas exchange. The nose and mouth form the entrance to the airways of a patient.

The airways consist of a series of branching tubes, which become narrower, shorter and more numerous as they penetrate deeper into the lung. The prime function of the lung is gas exchange, allowing oxygen to move from the air into the venous blood and carbon dioxide to move out. The trachea divides into right and left main bronchi, which further divide eventually into terminal bronchioles. The bronchi make up the conducting airways, and do not take part in gas exchange. Further divisions of the airways lead to the respiratory bronchioles, and eventually to the alveoli. The alveolated region of the lung is where the gas exchange takes place, and is referred to as the respiratory zone. See West, Respiratory Physiology—the essentials.

A range of respiratory disorders exist.

Obstructive Sleep Apnoea (OSA), a form of Sleep Disordered Breathing (SDB), is characterized by occlusion of the upper air passage during sleep. It results from a combination of an abnormally small upper airway and the normal loss of muscle tone in the region of the tongue, soft palate and posterior oropharyngeal wall during sleep. The condition causes the affected patient to stop breathing for periods typically of 30 to 120 seconds duration, sometimes 200 to 300 times per night. It often causes excessive daytime somnolence, and it may cause cardiovascular disease and brain damage. The syndrome is a common disorder, particularly in middle aged overweight males, although a person affected may have no awareness of the problem. See U.S. Pat. No. 4,944,310 (Sullivan).

Cheyne-Stokes Respiration (CSR) is a disorder of a patient's respiratory controller in which there are rhythmic alternating periods of waxing and waning ventilation, causing repetitive de-oxygenation and re-oxygenation of the arterial blood. It is possible that CSR is harmful because of the repetitive hypoxia. In some patients CSR is associated with repetitive arousal from sleep, which causes severe sleep disruption, increased sympathetic activity, and increased afterload. See U.S. Pat. No. 6,532,959 (Berthon-Jones).

Obesity Hyperventilation Syndrome (OHS) is defined as the combination of severe obesity and awake chronic hypercapnia, in the absence of other known causes for hypoventilation. Symptoms include dyspnea, morning headache and excessive daytime sleepiness.

Chronic Obstructive Pulmonary Disease (COPD) encompasses any of a group of lower airway diseases that have certain characteristics in common. These include increased resistance to air movement, extended expiratory phase of respiration, and loss of the normal elasticity of the lung. Examples of COPD are emphysema and chronic bronchitis. COPD is caused by chronic tobacco smoking (primary risk factor), occupational exposures, air pollution and genetic factors. Symptoms include: dyspnoea on exertion, chronic cough and sputum production.

Neuromuscular Disease (NMD) is a broad term that encompasses many diseases and ailments that impair the functioning of the muscles either directly via intrinsic muscle pathology, or indirectly via nerve pathology. Some NMD patients are characterised by progressive muscular impairment leading to loss of ambulation, being wheelchair-bound, swallowing difficulties, respiratory muscle weakness and, eventually, death from respiratory failure. Neuromuscular disorders can be divided into rapidly progressive and slowly progressive: (i) Rapidly progressive disorders: Characterised by muscle impairment that worsens over months and results in death within a few years (e.g. Amyotrophic lateral sclerosis (ALS) and Duchenne muscular dystrophy (DMD) in teenagers); (ii) Variable or slowly progressive disorders: Characterised by muscle impairment that worsens over years and only mildly reduces life expectancy (e.g. Limb girdle, Facioscapulohumeral and Myotonic muscular dystrophy). Symptoms of respiratory failure in NMD include: increasing generalised weakness, dysphagia, dyspnoea on exertion and at rest, fatigue, sleepiness, morning headache, and difficulties with concentration and mood changes.

Chest wall disorders are a group of thoracic deformities that result in inefficient coupling between the respiratory muscles and the thoracic cage. The disorders are usually characterised by a restrictive defect and share the potential of long term hypercapnic respiratory failure. Scoliosis and/or kyphoscoliosis may cause severe respiratory failure. Symptoms of respiratory failure include: dyspnoea on exertion, peripheral oedema, orthopnoea, repeated chest infections, morning headaches, fatigue, poor sleep quality and loss of appetite.

Otherwise healthy individuals may take advantage of systems and devices to prevent respiratory disorders from arising.

2.2.1 Systems

One known product used for treating sleep disordered breathing is the S9 Sleep Therapy System, manufactured by ResMed.

2.2.2 Therapy

Nasal Continuous Positive Airway Pressure (CPAP) therapy has been used to treat Obstructive Sleep Apnea (OSA). The hypothesis is that continuous positive airway pressure acts as a pneumatic splint and may prevent upper airway occlusion by pushing the soft palate and tongue forward and away from the posterior oropharyngeal wall.

Non-invasive ventilation (NIV) has been used to treat OHS, COPD, MD and Chest Wall disorders.

2.2.3 Patient Interface

The application of a supply of air at positive pressure to the entrance of the airways of a patient is facilitated by the use of a patient interface, such as a nasal mask, full-face mask or nasal pillows. A range of patient interface devices are known, however a number of them suffer from being one or more of obtrusive, aesthetically undesirable, poorly fitting, difficult to use and uncomfortable especially when worn for long periods of time or when a patient is unfamiliar with a system. Masks designed solely for aviators, as part of personal protection equipment or for the administration of anaesthetics may be tolerable for their original application, but nevertheless be undesirably uncomfortable to be worn for extended periods, for example, while sleeping.

2.2.4 PAP Device

PAP devices are used to deliver positive airway pressure in many forms. For example, a positive pressure level may be maintained across the inspiratory and expiratory levels of the patient's breathing cycle at an approximately constant level. Alternatively, pressure levels may be adjusted to change synchronously with the patient's breathing cycle. For example, pressure may be set at one level during inspiration and another lower level during expiration for patient comfort. Such a pressure treatment system may be referred to as bi-level. Alternatively, the pressure levels may be continuously adjusted to smoothly replicate changes in the patient's breathing cycle. A lower pressure setting during expiration may generally be referred to as expiratory pressure relief.

In providing such changes to pressure and/or detecting conditions for making adjustments to the treatment pressure, it can be helpful to have a measure or estimation of patient respiratory flow or total volumetric flow. For example, a flow signal may be utilized to detect when a patient changes from inspiration to expiration for determining when to deliver expiratory pressure treatment settings or inspiratory pressure treatment settings. Similarly, the flow signal may be utilized to detect patient flow limitation for purposes of making treatment pressure adjustments. Such adjustments are illustrated in the U.S. Pat. No. 5,704,345. For these purposes, a measured flow signal may be derived from a flow sensor such as a differential pressure transducer or pnuemotachograph. Alternatively, the flow signal may be estimated in the absence of a flow sensor.

2.2.5 Humidifier

Respiratory apparatuses commonly have the ability to alter the humidity of the breathable gas in order to reduce drying of the patient's airway and consequent patient discomfort and associated complications. The use of a humidifier placed between the flow generator and the patient interface produces humidified gas that minimizes drying of the nasal mucosa and increases patient airway comfort. In addition in cooler climates, warm air applied generally to the face area in and about the patient interface is more comfortable than cold air.

Many humidifier types are available, although the most convenient form is one that is either integrated with or configured to be coupled to the relevant respiratory apparatus. While passive humidifiers can provide some relief, generally a heated humidifier is required to provide sufficient humidity and temperature to the air so that the patient will be comfortable. Humidifiers typically comprise a water reservoir or tub having a capacity of several hundred milliliters (ml), a heating element for heating the water in the reservoir, a control to enable the level of humidification to be varied, a gas inlet to receive gas from the flow generator, and a gas outlet adapted to be connected to a patient conduit that delivers the humidified gas to the patient's mask.

Typically, the heating element is incorporated in a heater plate which sits under, and is in thermal contact with, the water tub. Thus, heat is transferred from the heater plate to the water reservoir primarily by conduction.

In the prior art, additional components have been used to improve thermal contact between the water reservoir and the heater plate. One example is the use of spring elements, which are used to connect the heater plate to the humidifier body, as described in U.S. Pat. No. 4,203,027, thereby pushing the heater plate towards the water reservoir. Another example is a humidifier with a lid wherein a compressible elastomer seal is provided on the lid, as described in WO2010/031126. In this example, when the lid is in its closed position the seal engages against the water reservoir and pushes it against the heater plate.

Another aspect of a prior art humidifier water reservoir is that over-filling and/or tilting of the water reservoir may result in the flow of water back into the PAP device. The introduction of elongated inlets such as those disclosed in WO 2004/026382 has reduced the risk of spillage due to tilt, however the water reservoir still can be over-filled, and when this occurs it may reduce the effectiveness of such spill-protection system. As a result, such prior art humidifier water reservoirs have included a water filling indication mark to reduce occurrence of such over-filling.

3 BRIEF SUMMARY OF THE INVENTION

The present technology is directed towards providing medical devices used in the diagnosis, amelioration, treatment, or prevention of respiratory disorders having one or more of improved comfort, cost, efficacy, ease of use and manufacturability.

A first aspect of the present technology relates to apparatus used in the diagnosis, amelioration, treatment or prevention of a respiratory disorder.

Another aspect of the present technology relates to methods used in the diagnosis, amelioration, treatment or prevention of a respiratory disorder.

One form of the present technology comprises a humidifier reservoir or tub comprising an internal variable portion, which generates a force pushing the humidifier reservoir towards the heater plate when the humidifier reservoir is engaged with the humidifier. The variable portion may also include a seal.

Another aspect of one form of the present technology is a humidifier reservoir comprising a variable element which is compressed and generates a force pushing the humidifier reservoir towards the heater plate when the humidifier reservoir is engaged with the humidifier.

One form of the present technology comprises a humidifier reservoir wherein when the humidifier reservoir is engaged with the humidifier, the introduction of therapy pressure improves thermal engagement of the humidifier reservoir with the heater plate.

Another aspect of one form of the present technology is a humidifier reservoir comprising a means of using therapy pressure that is introduced within the humidifier reservoir to generate a force between the humidifier reservoir and the heater plate to improve thermal coupling between the humidifier reservoir and the heater plate.

One form of the present technology comprises a humidifier reservoir comprising an over-filling protection element configured to indicate over-filling.

In one form of the present technology the over-filling protection element may include at least one orifice in a wall of the reservoir. The at least one orifice defines an egress path of water when the predetermined maximum volume of water is exceeded.

In another form of the present technology the over-filling protection element may include a sloped profile in the side profile of a wall of the reservoir that defines an egress path of water when the predetermined maximum volume of water is exceeded.

Another aspect of one form of the present technology is a humidifier reservoir comprising an over-filling protection element to prevent the humidifier reservoir from filling beyond a predetermined or maximum capacity.

One form of the present technology comprises a humidifier reservoir comprising an inlet and outlet arranged to prevent spillage of water from the reservoir back through the inlet and/or outlet.

Of course, portions of the aspects may form sub-aspects of the present invention. Also, various ones of the sub-aspects and/or aspects may be combined in various manners and also constitute additional aspects or sub-aspects of the present invention.

Other features of the technology will be apparent from consideration of the information contained in the following detailed description, abstract, drawings and claims.

4 BRIEF DESCRIPTION OF THE SEVERAL VIEWS OF THE DRAWINGS

The present technology is illustrated by way of example, and not by way of limitation, in the figures of the accompanying drawings, in which like reference numerals refer to similar elements including:

4.1 Treatment Systems

FIG. 1a shows a system in accordance with the present technology. A patient 1000 wearing a patient interface 3000, receives a supply of air at positive pressure from a positive airway pressure (PAP) device 4000. Air from the PAP device is humidified in a humidifier 5000, and passes along an air circuit 4170 to the patient 1000.

4.2 Therapy

4.2.1 Respiratory System

Figure 1A:
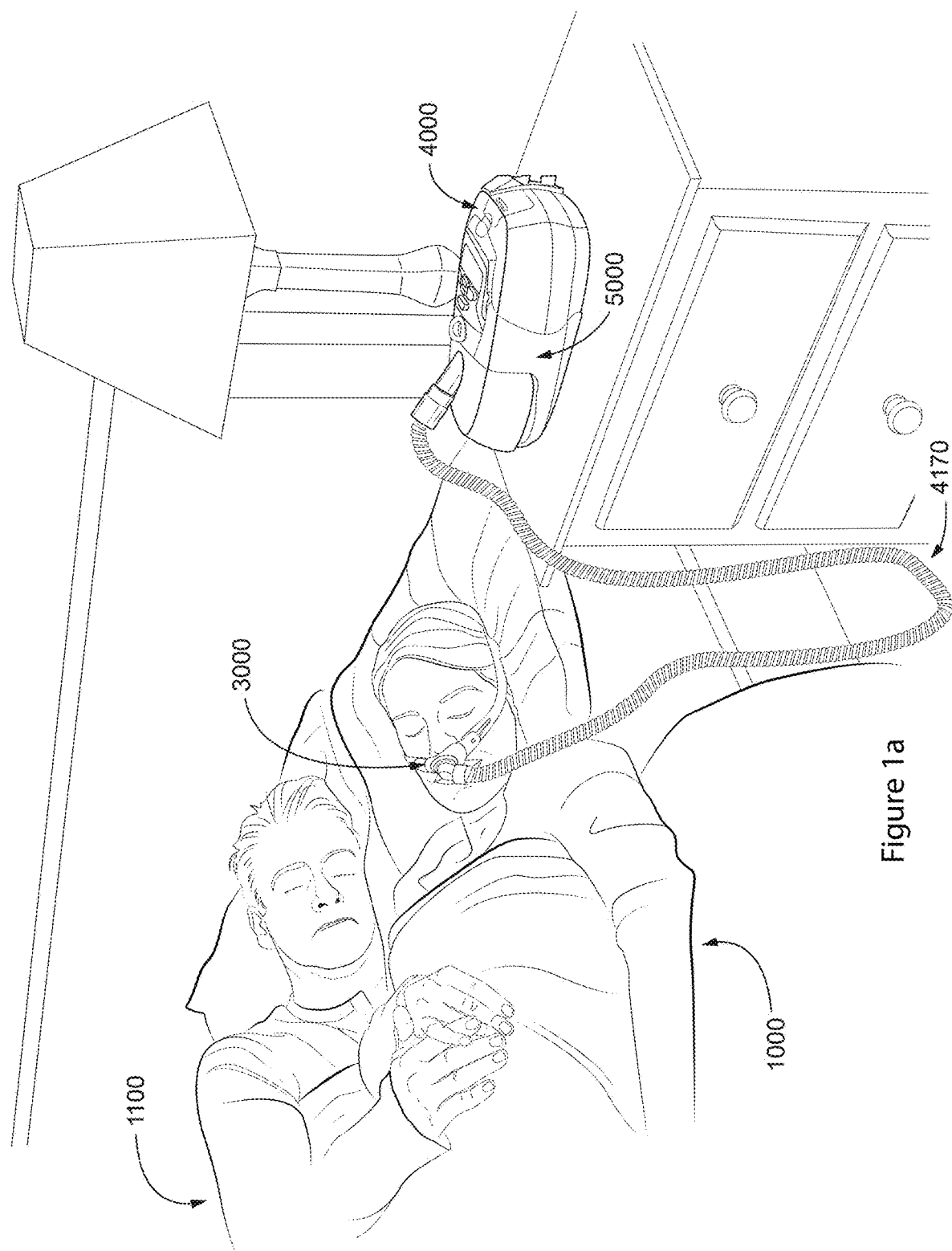
FIG. 1b shows a PAP device in use on a patient with a nasal mask.
FIG. 1c shows a PAP device in use on a patient with a full-face mask.
Figure 1B:
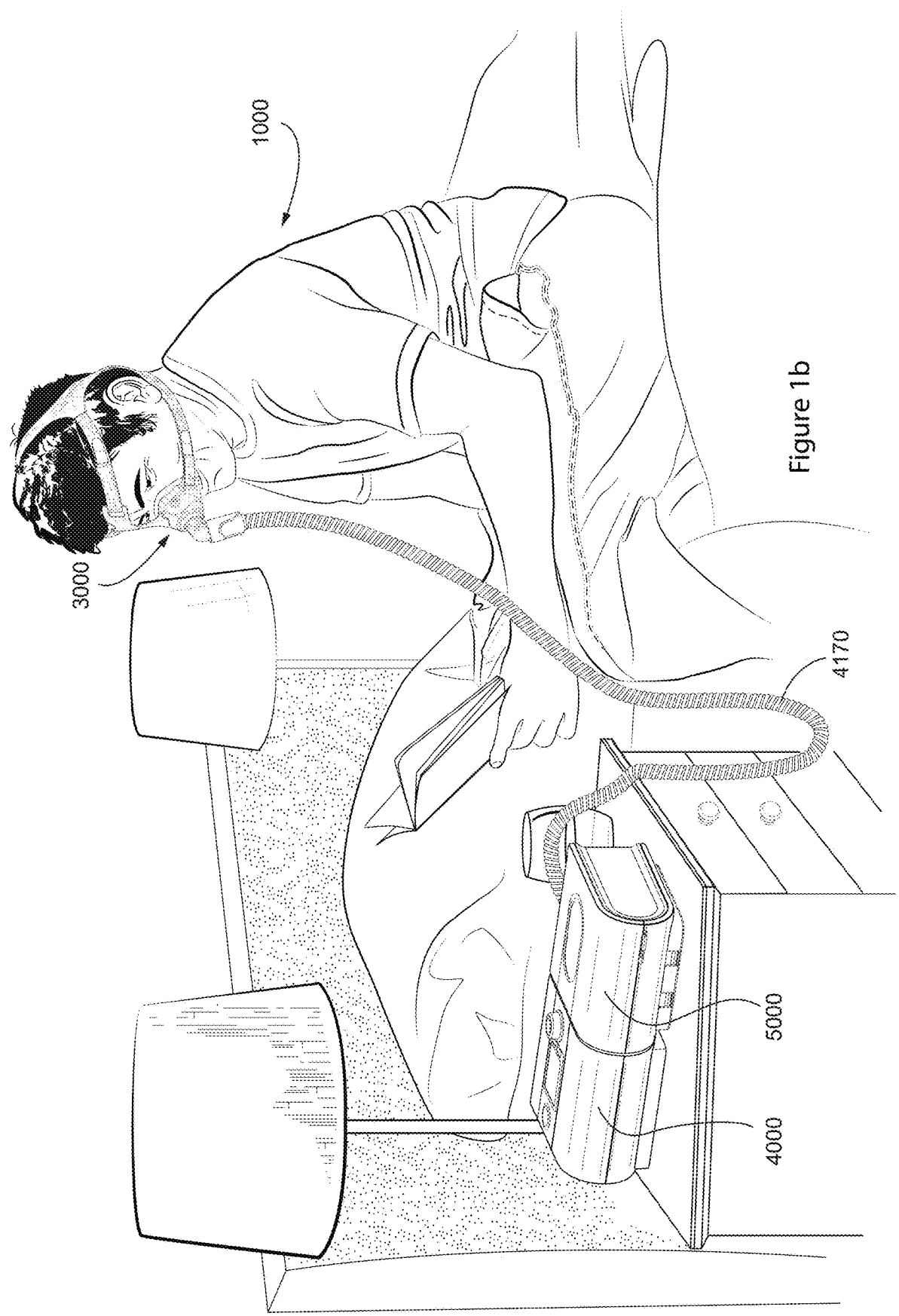
Figure 1C:
Figure 2A:
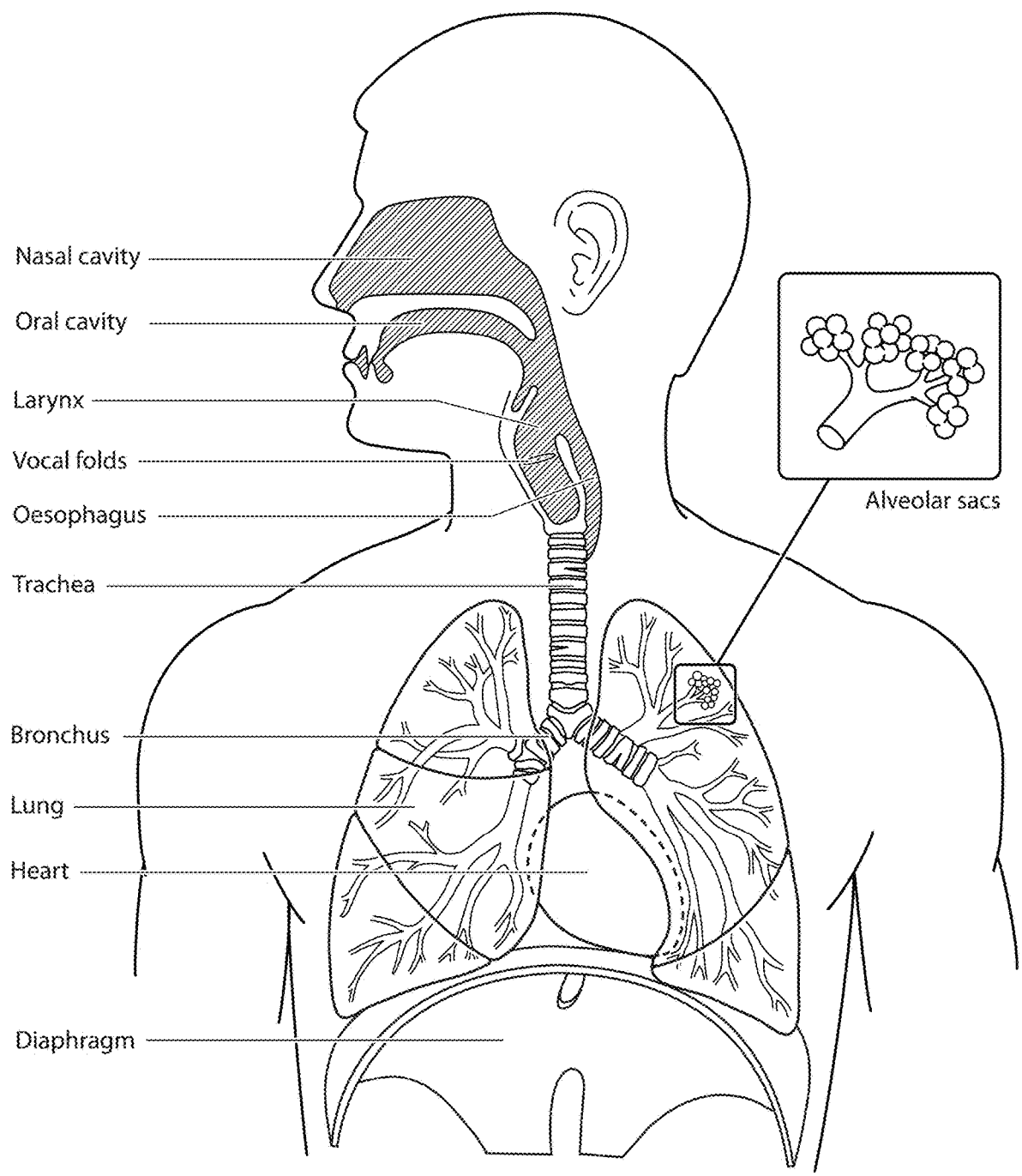

FIG. 2a shows an overview of a human respiratory system including the nasal and oral cavities, the larynx, vocal folds, oesophagus, trachea, bronchus, lung, alveolar sacs, heart and diaphragm.

Figure 2B:
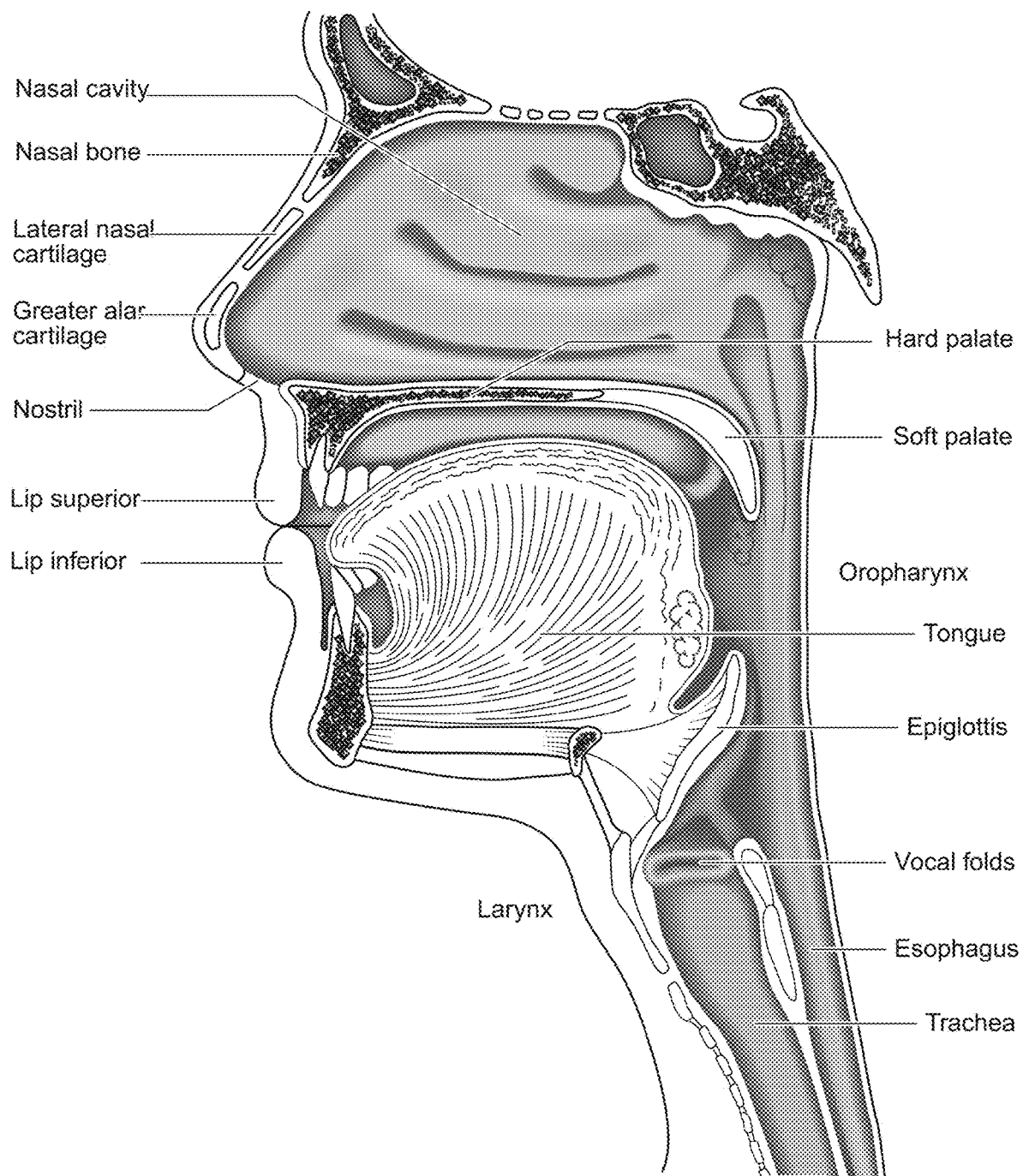

FIG. 2b shows a view of a human upper airway including the nasal cavity, nasal bone, lateral nasal cartilage, greater alar cartilage, nostril, lip superior, lip inferior, larynx, hard palate, soft palate, oropharynx, tongue, epiglottis, vocal folds, oesophagus and trachea.

4.3 Patient Interface

Figure 3A:
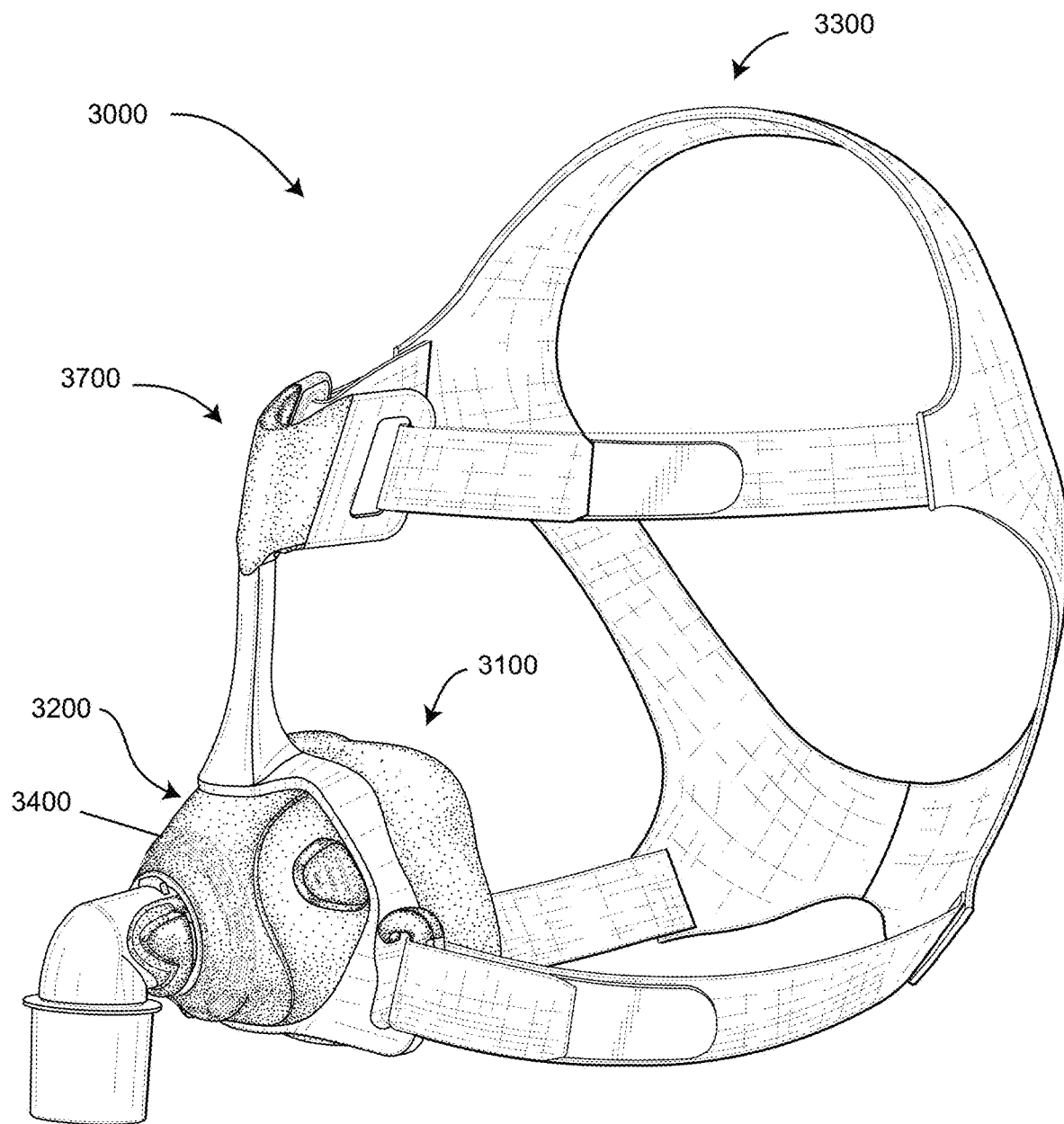

FIG. 3a shows a patient interface in accordance with one form of the present technology.

4.4 Pap Device

Figure 4A:
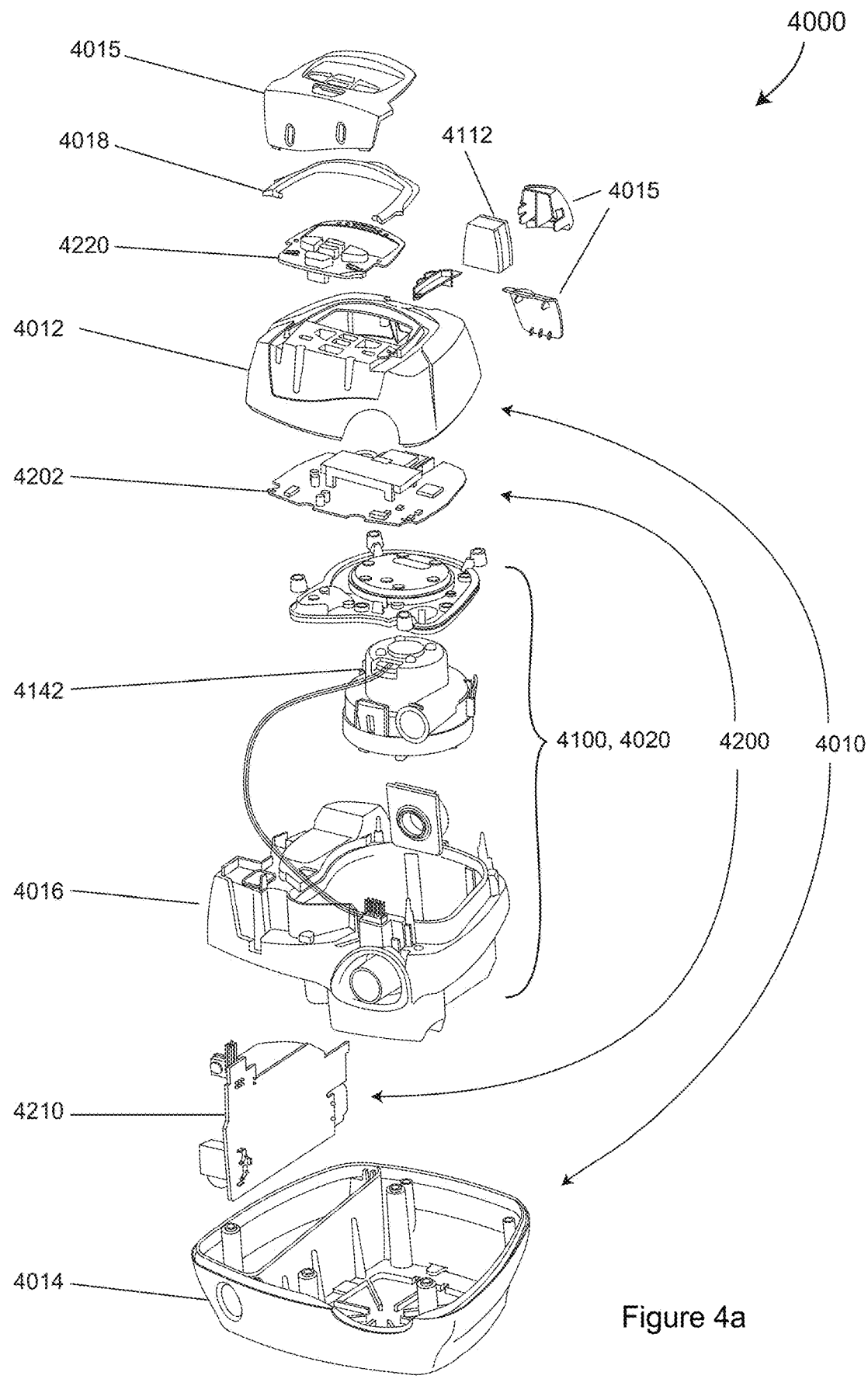

FIG. 4a shows a PAP device in accordance with one form of the present technology.

Figure 4B:
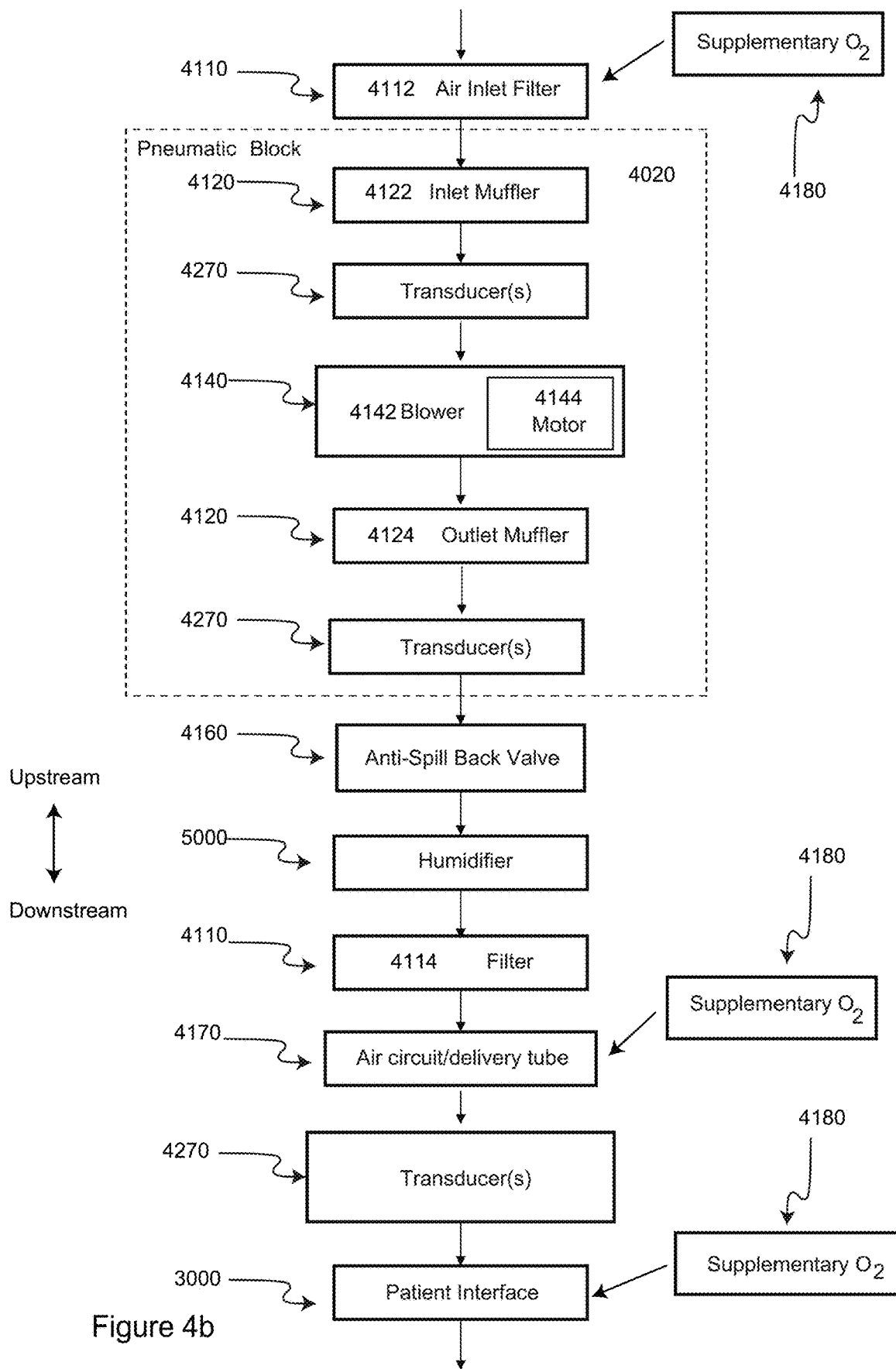

FIG. 4b shows a schematic diagram of the pneumatic components of a PAP device in accordance with one form of the present technology. The directions of upstream and downstream are indicated.

It should be understood that a number of components, such as supplementary $O_2$ 4180, anti-spill back valve 4160, or the transducer(s) 4270 are optional. Also, in an alternative arrangement the humidifier 5000 may be placed in alternative locations for example, upstream of the pneumatic block 4020.

4.5 Humidifier

Figure 5A:
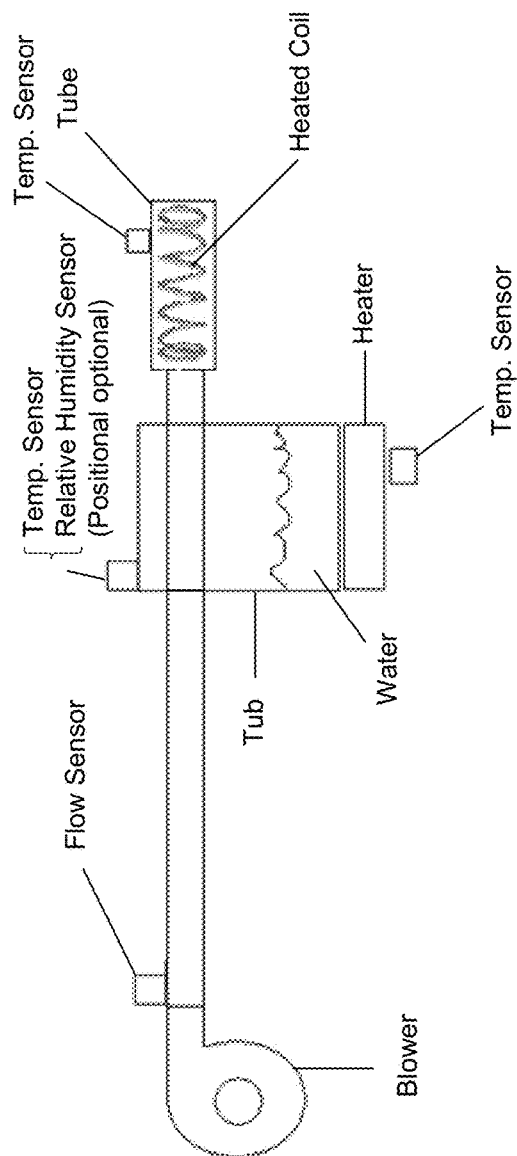
Figure 5B:
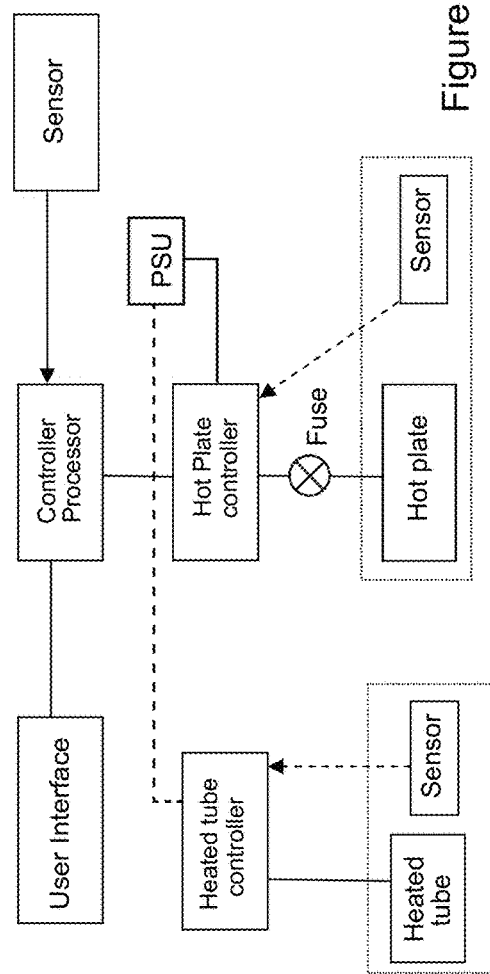

FIG. 5a shows a simplified representation of a humidifier connected to a blower and a patient conduit FIG. 5b shows a schematic of a humidifier.

4.6 Breathing Waveforms

Figure 6A:
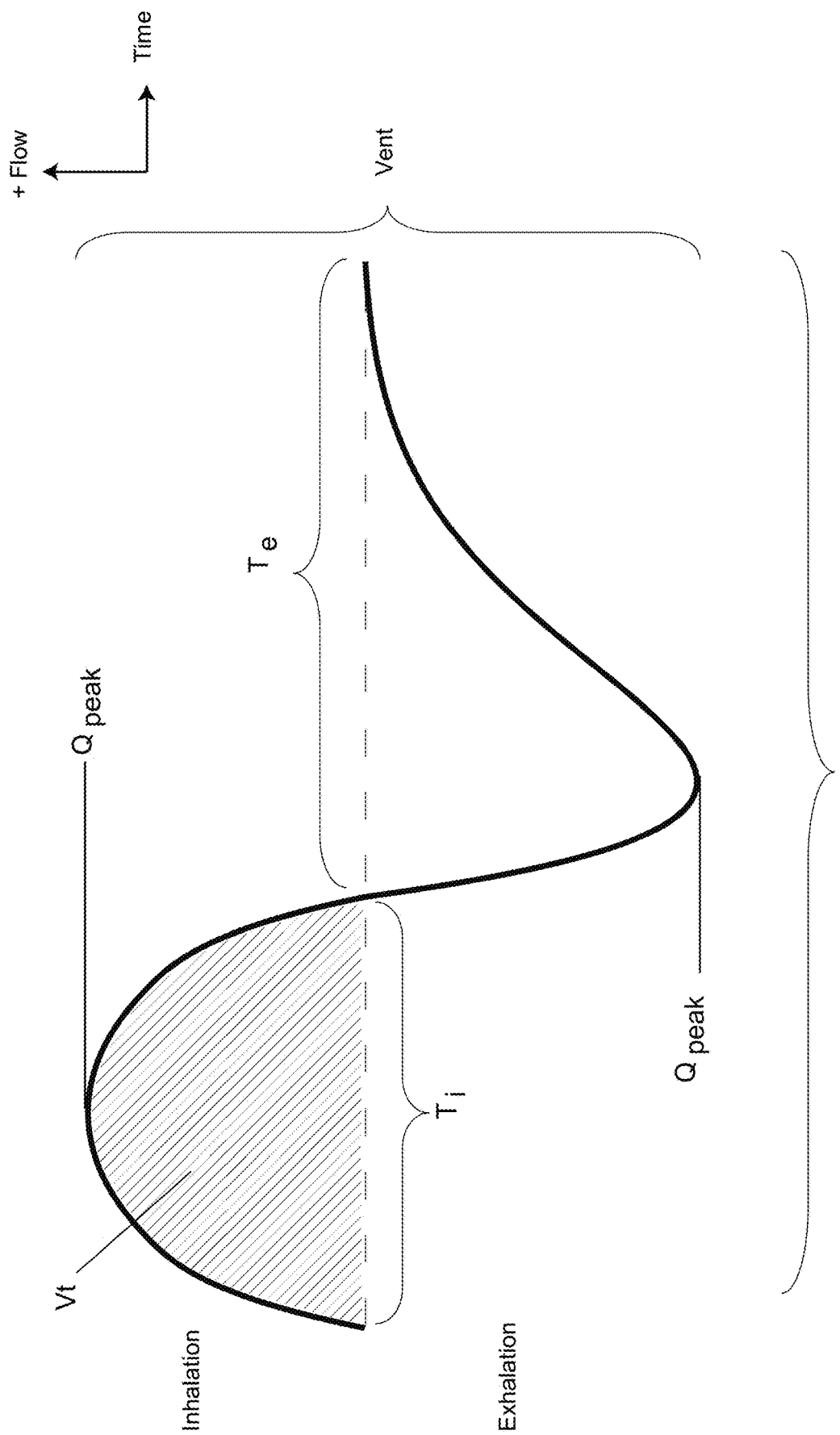

FIG. 6a shows a model typical breath waveform of a person while sleeping, the horizontal axis is time, and the vertical axis is flow. While the parameter values may vary, a typical breath may have the following approximate values: tidal volume, Vt, 0.5 L, inhalation time, Ti, 1.6 s, peak inspiratory flow, Qpeak, 0.4 L/s, exhalation time, Te, 2.4 s, peak expiratory flow, Qpeak, −0.5 L/s. The total duration of the breath, Ttot, is about 4 s. The person typically breathes at a rate of about 15 breaths per minute (BPM), with Ventilation, Vent, about 7.5 L/s. A typical duty cycle, the ratio of Ti to Ttot is about 40%.

4.7 Pap Device with a Humidifier

Figure 7:
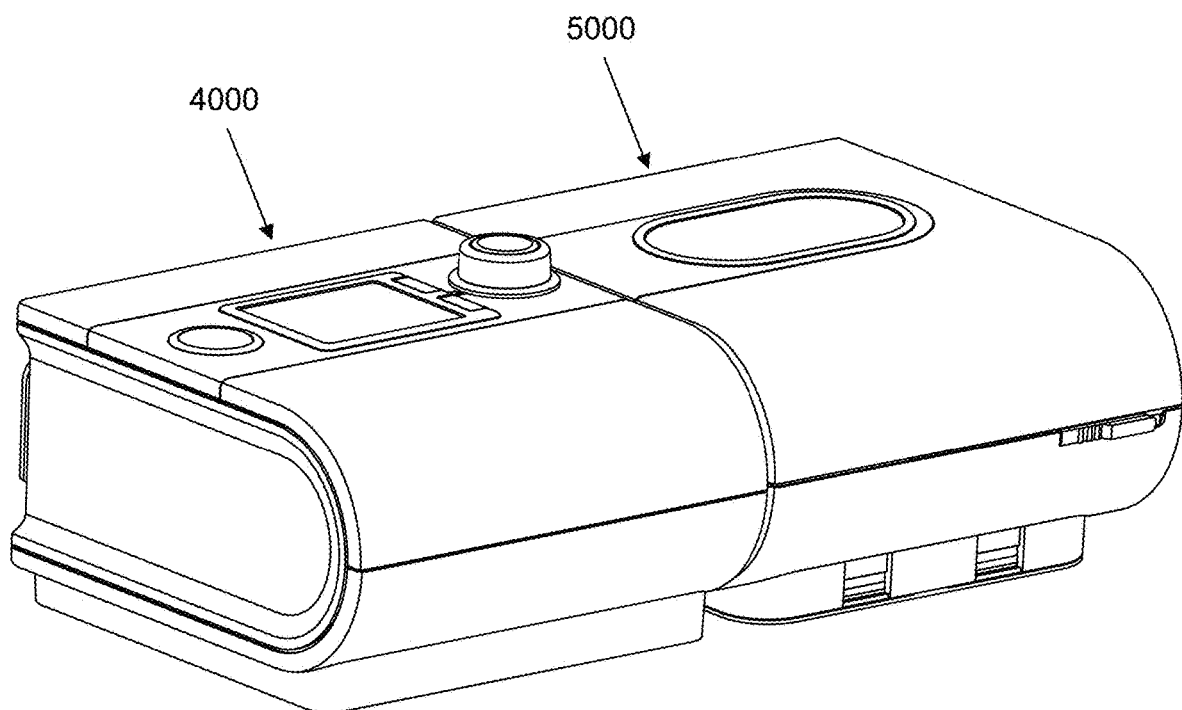

FIG. 7 shows a prior art example of a PAP device 4000 and a humidifier 5000.

Figure 8:
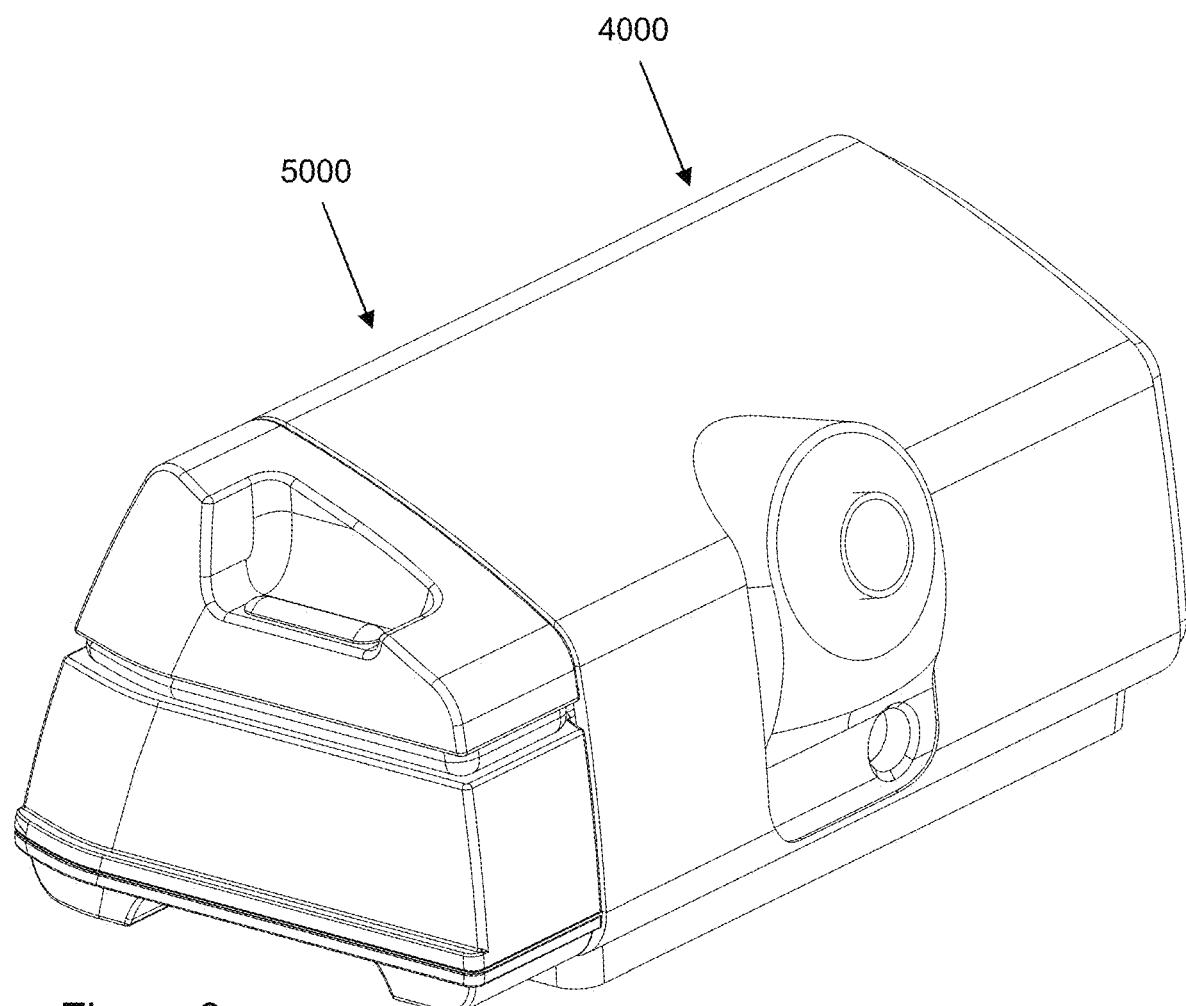

FIG. 8 shows an example of the present technology, showing a PAP device 4000 and an integrated humidifier 5000.

Figure 9:
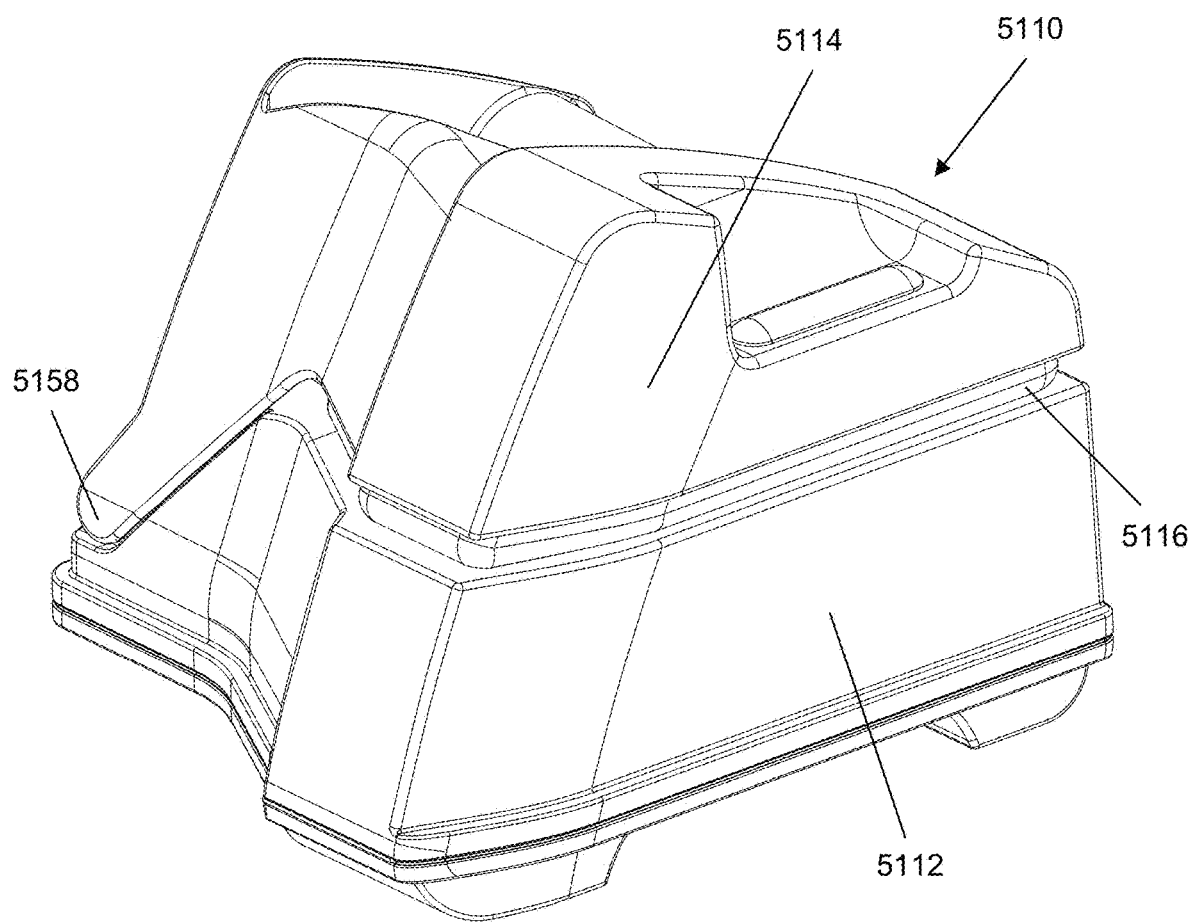
Figure 10:
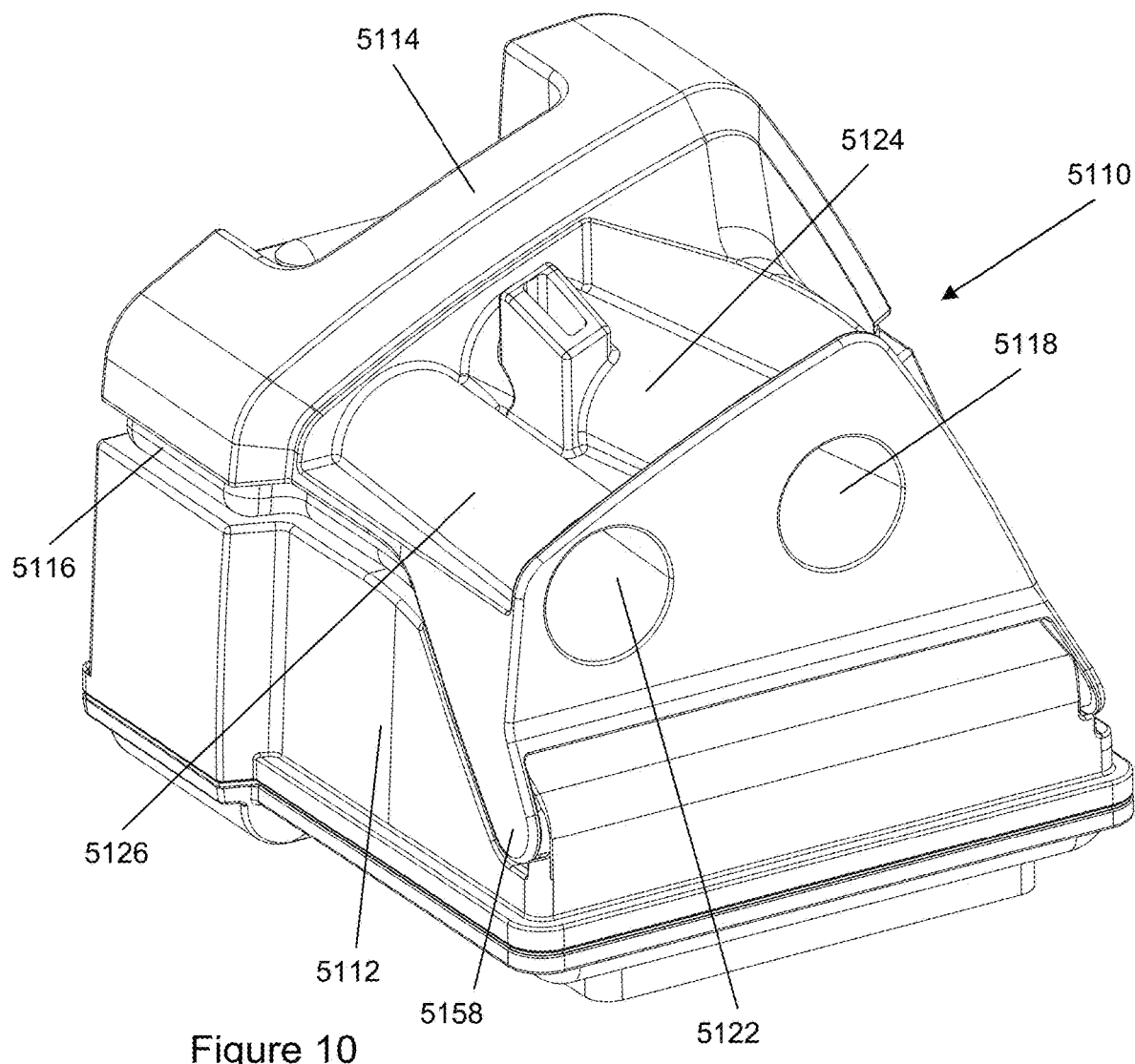
Figure 11:
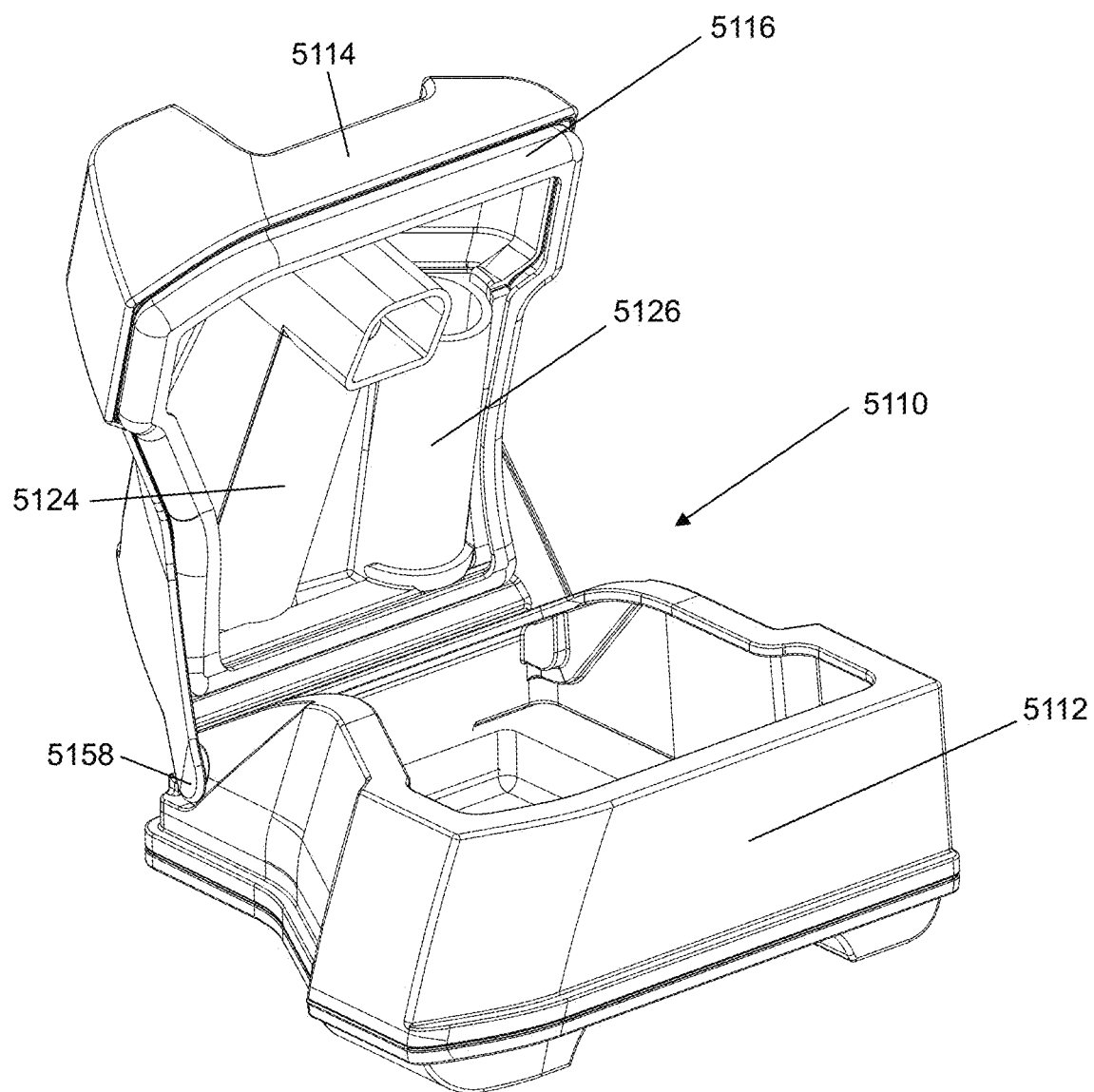
Figure 12:
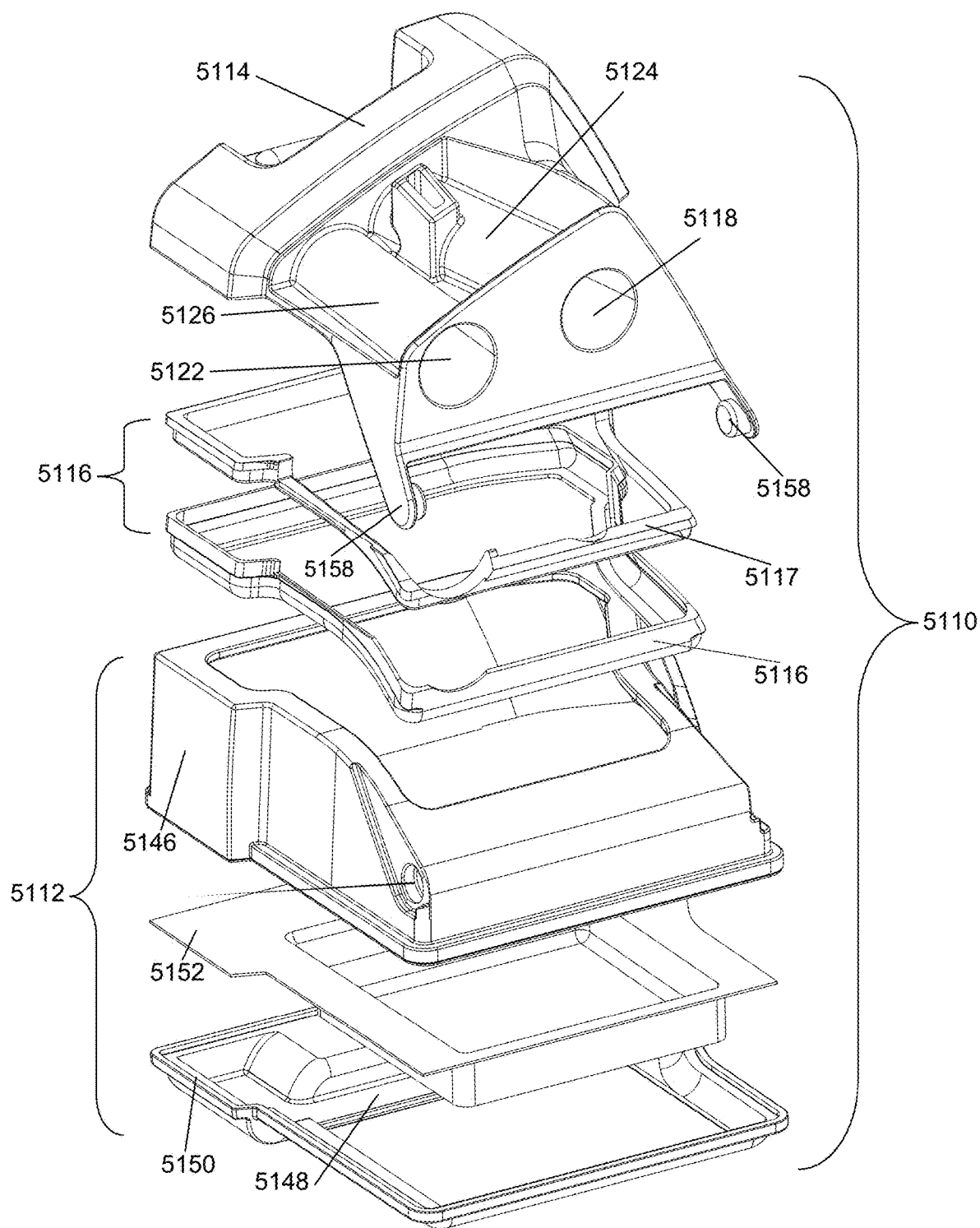

FIGS. 9-12 show various views of a humidifier reservoir 5110 in accordance with one aspect of present technology, wherein FIG. 9-10 show the humidifier reservoir 5110 in a 'closed' configuration, FIG. 11 shows the humidifier reservoir 5110 in an 'open' configuration, and FIG. 12 is an exploded view of the humidifier reservoir 5110.

FIGS. 13-16 show the humidifier 5000 from various perspectives, in particular demonstrating the engagement of the humidifier reservoir 5110 with the reservoir dock 5130.

Figure 17:
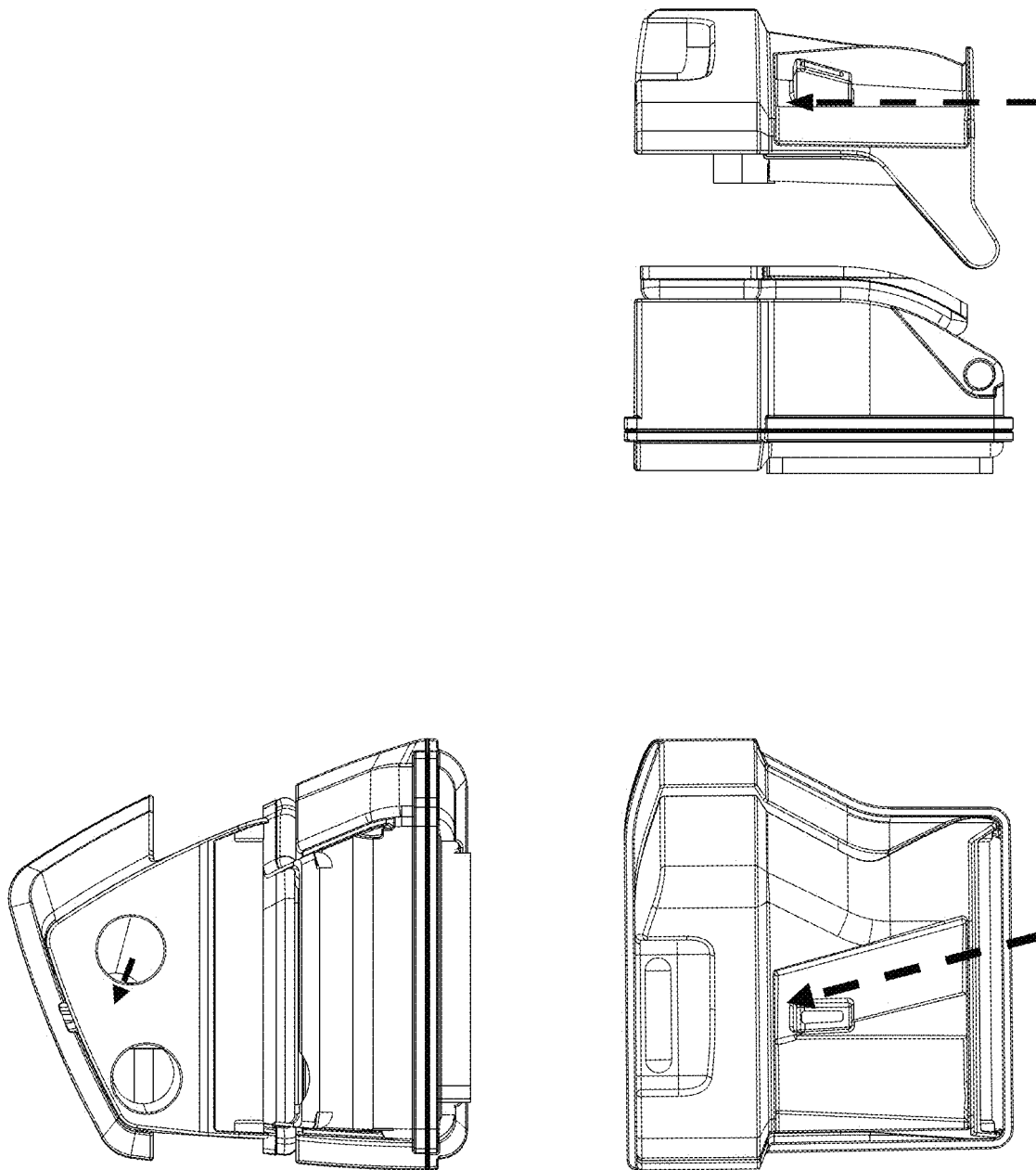
Figure 18:
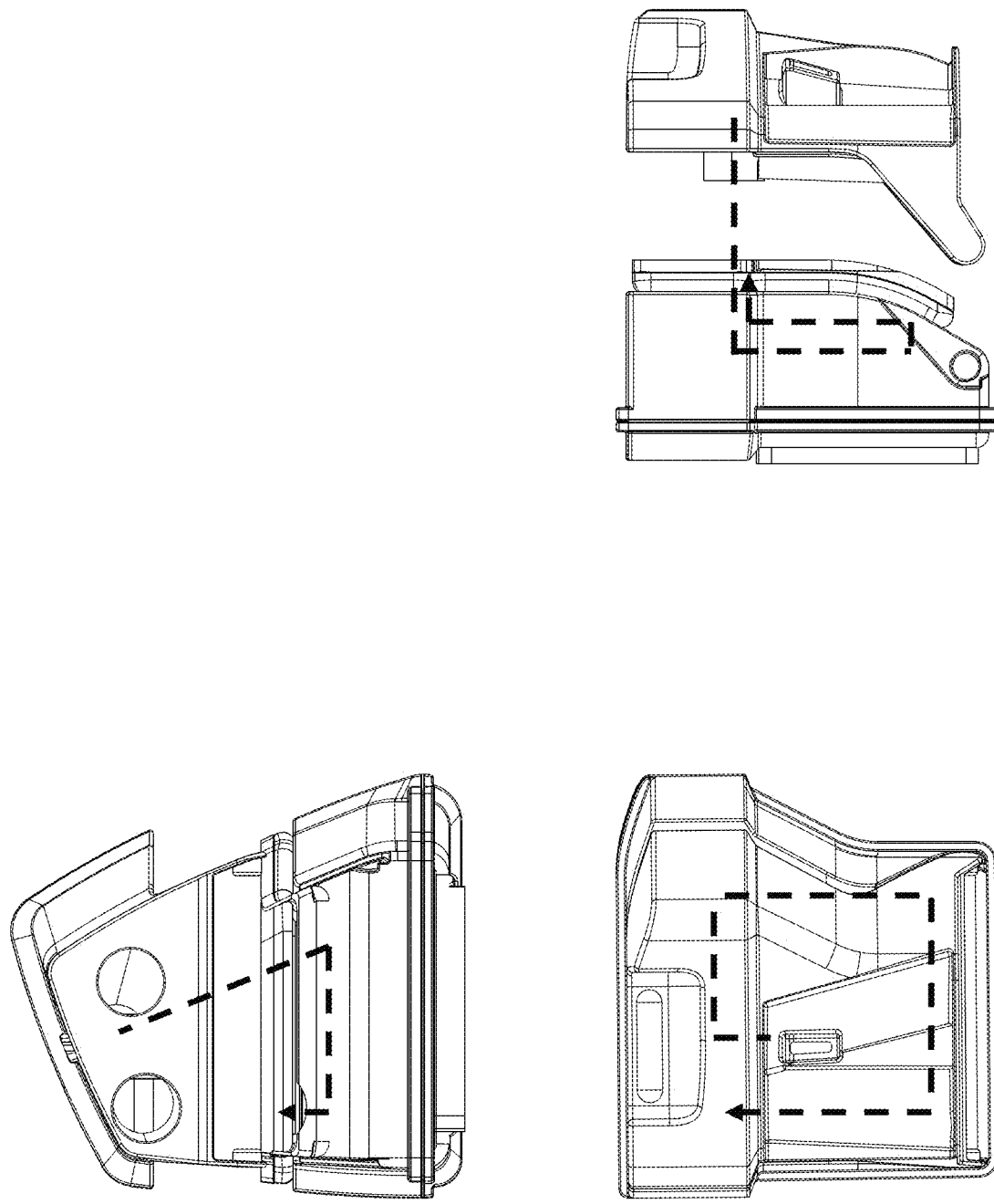
Figure 19:
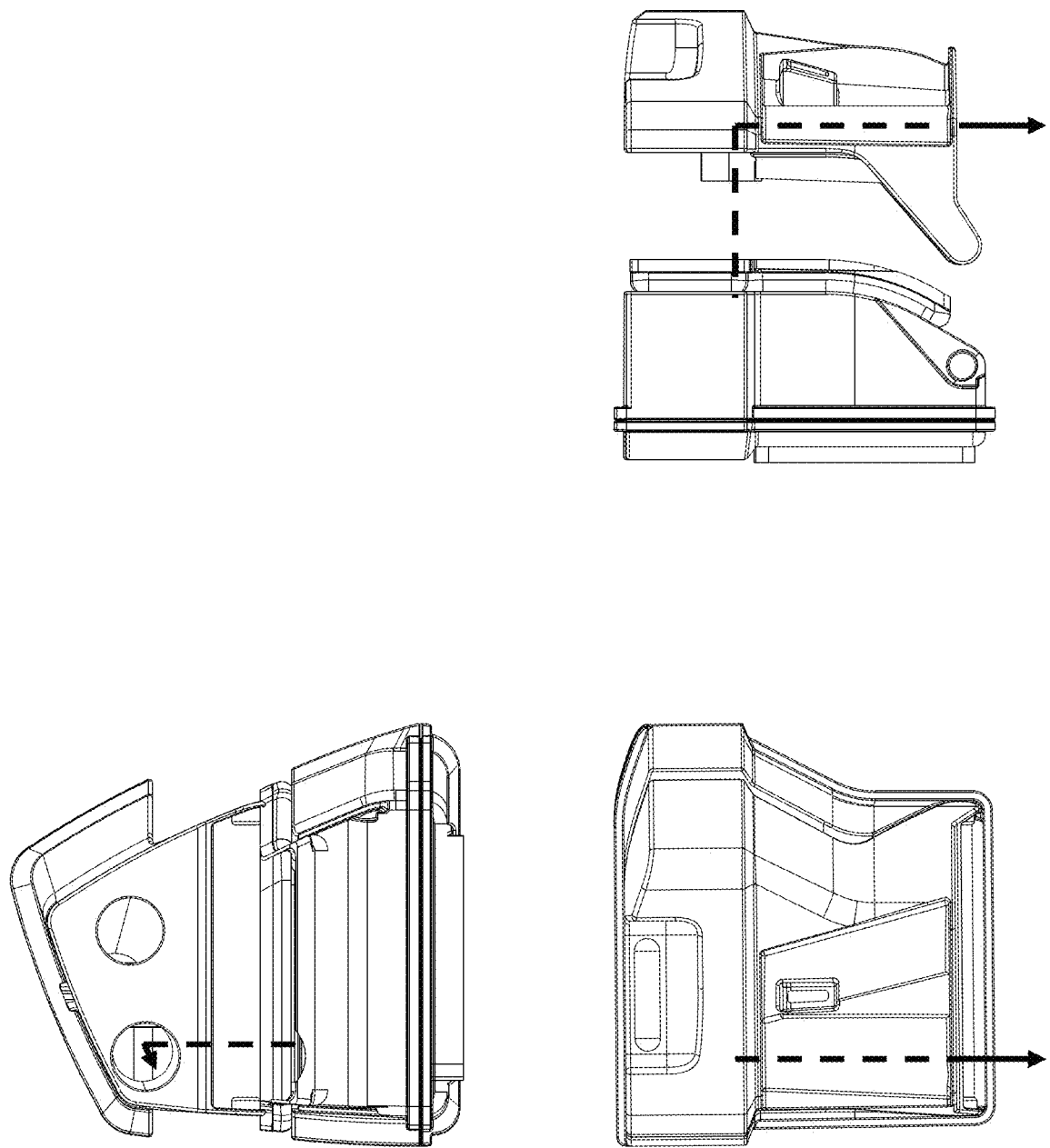

FIGS. 17-19 show a time-lapse chart of an exemplary flow path of gas as it enters the humidifier reservoir 5110 through the inlet 5118 and exits through the outlet 5122 after traversing through the inside of the humidifier reservoir 5110.

Figure 20:
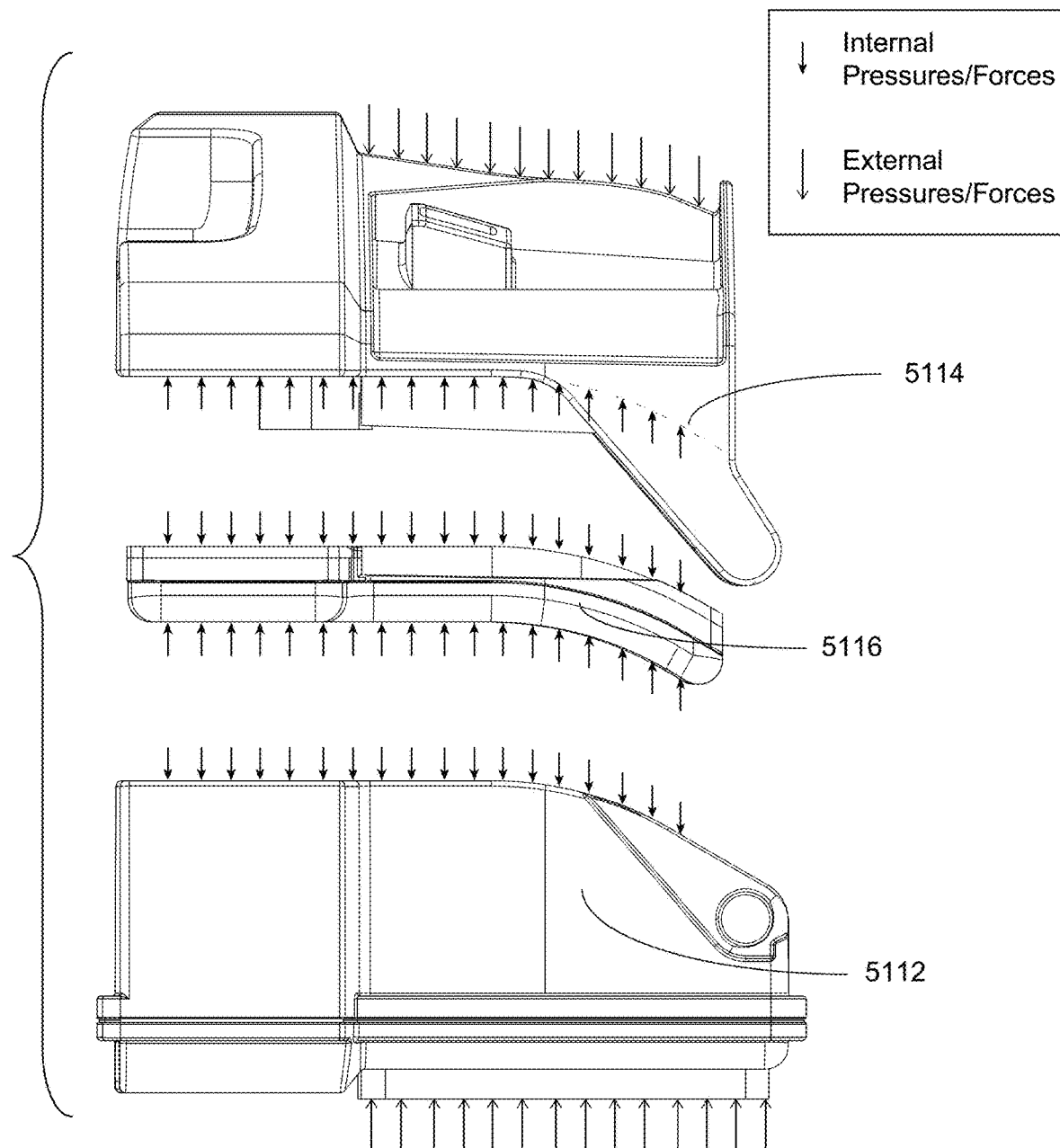
Figure 21:
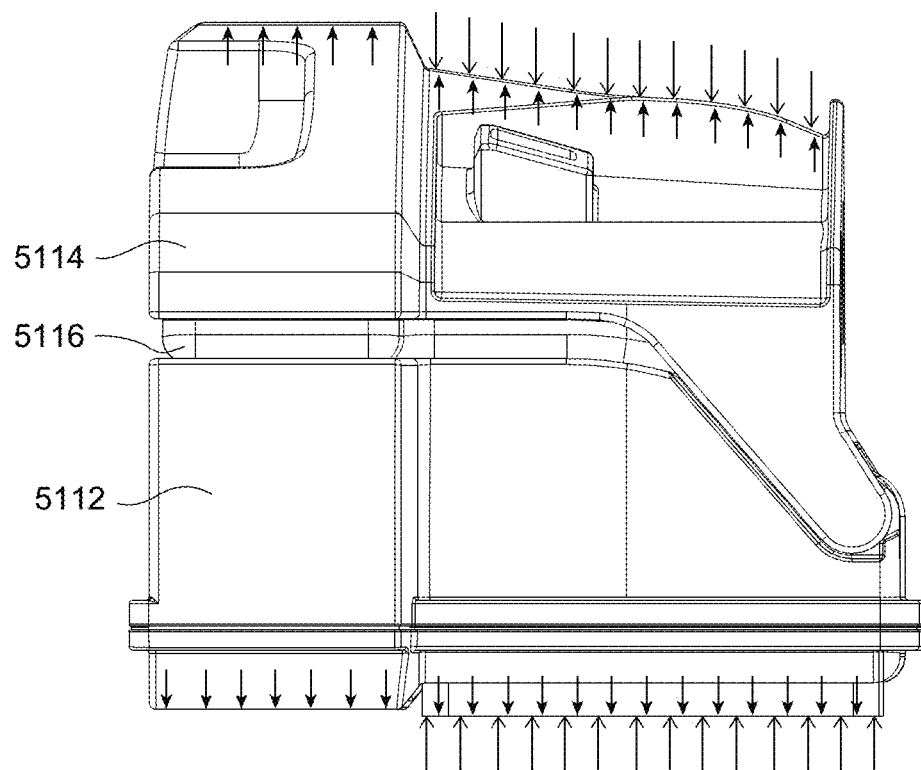

FIGS. 20-21 show exemplary distributions of pressure/force in the humidifier reservoir 5110 in various configurations.

FIGS. 22-29 show varying configurations of the reservoir lid 5114, in particular variations in configurations of the inlet tube 5124 and the outlet tube 5126 according to aspects of the present technology.

Figure 30A:
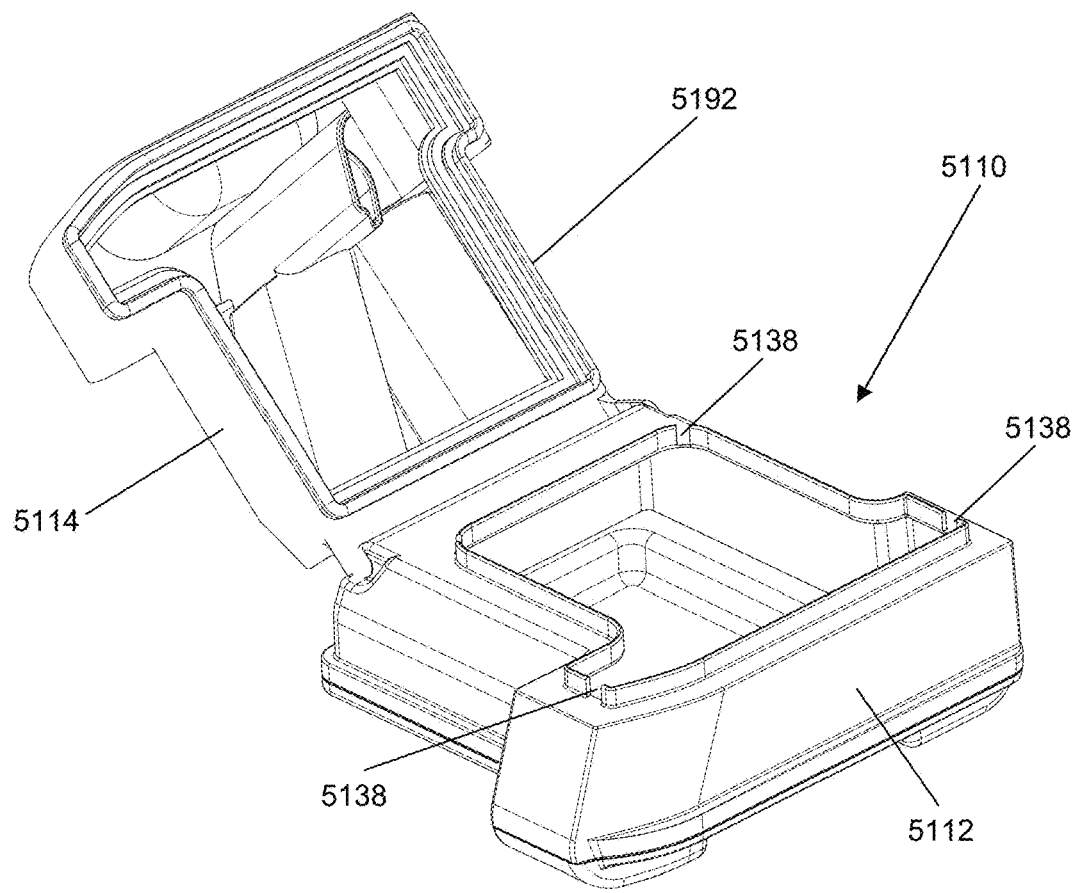
Figure 30B:
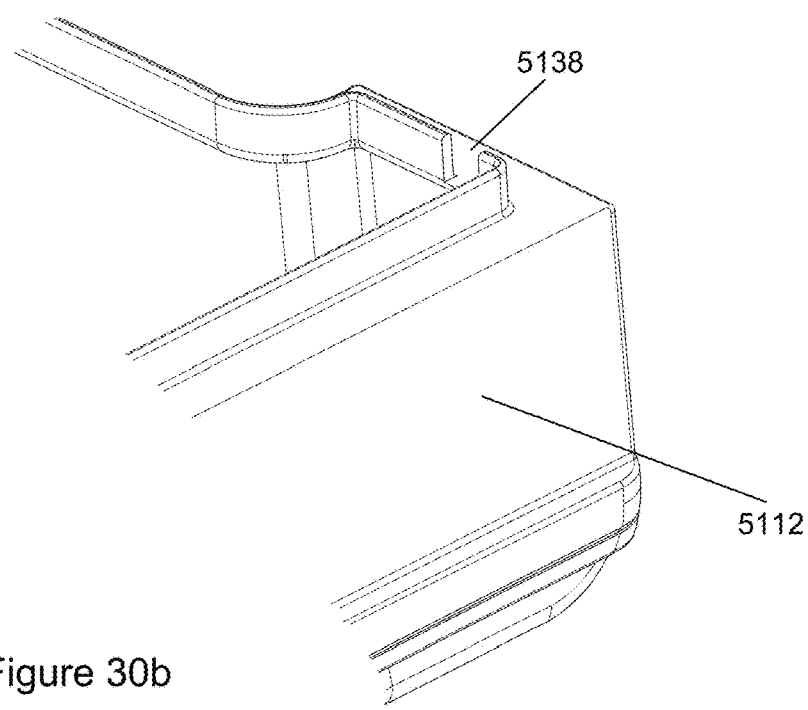

FIGS. 30a and 30b show the humidifier reservoir 5110 and in particular they aim to show the orifice 5138 according to an example of the present technology.

Figure 30C:
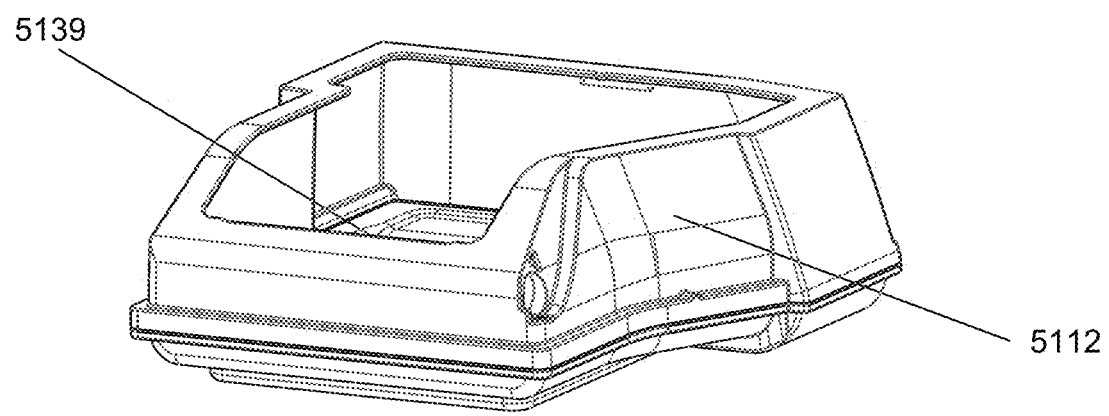
Figure 30D:
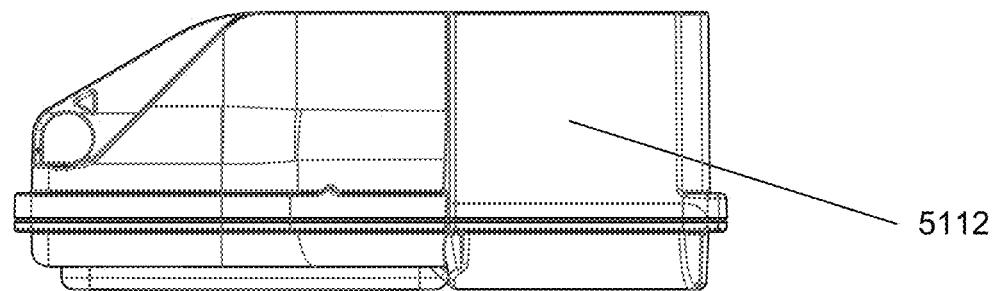

FIGS. 30c and 30d show the humidifier base 5112 and in particular the sloped profile 5139 according to an example of the present technology.

Figure 31:
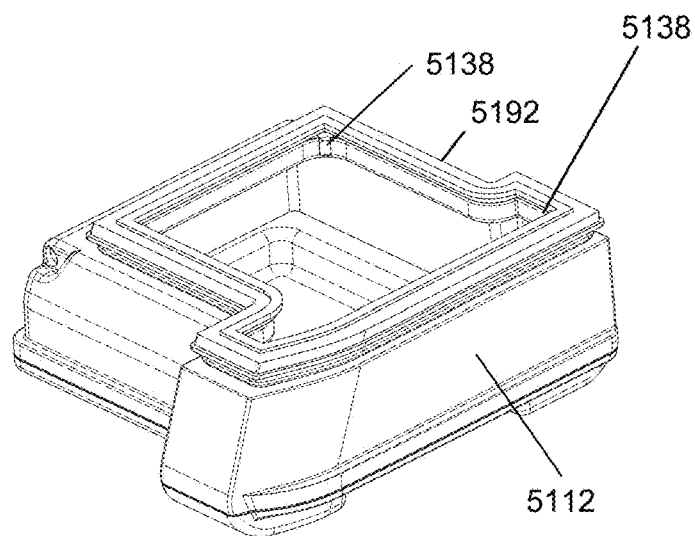

FIG. 31 shows the humidifier reservoir 5110 and in particular the orifice 5138 according to an example of the present technology.

Figure 32:
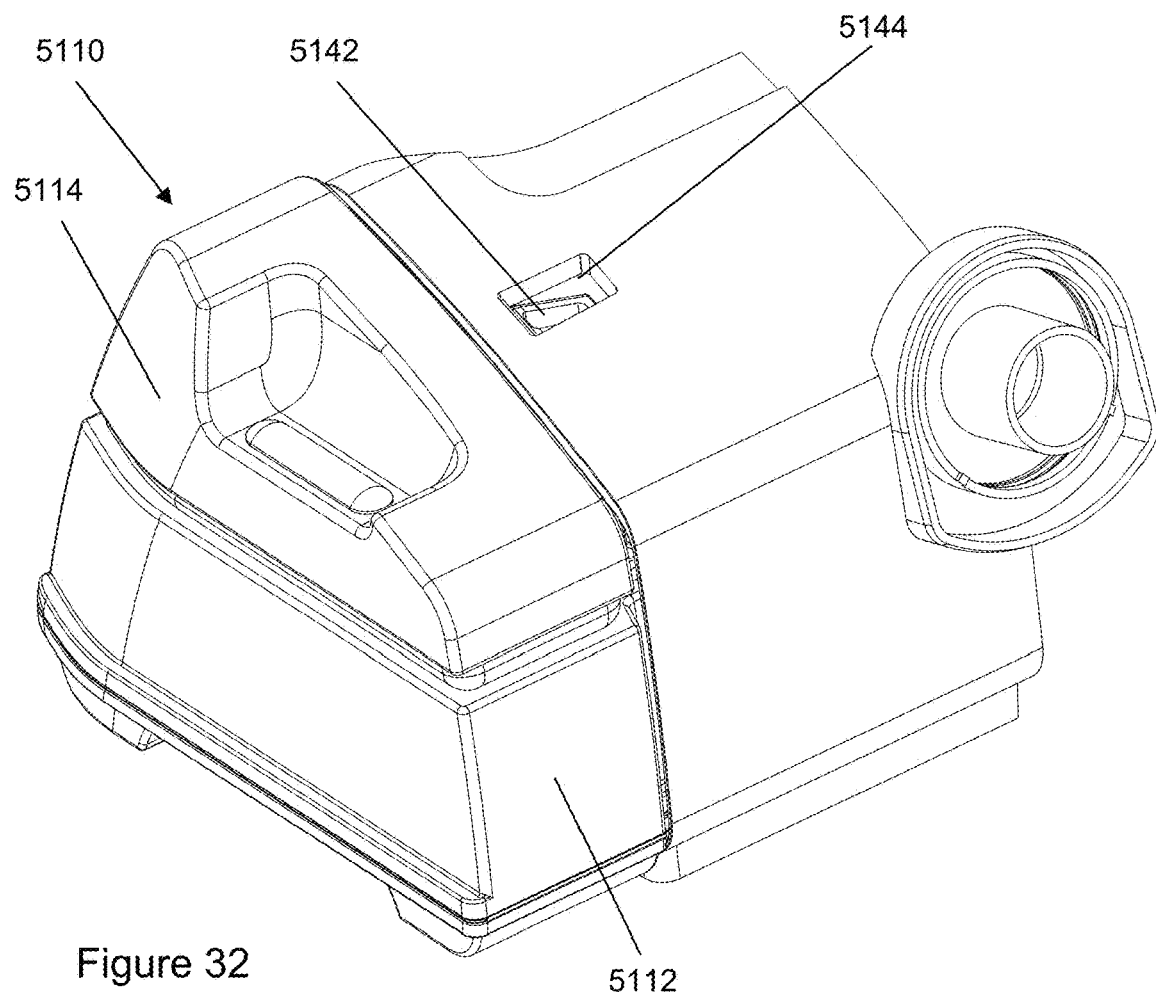
Figure 33:
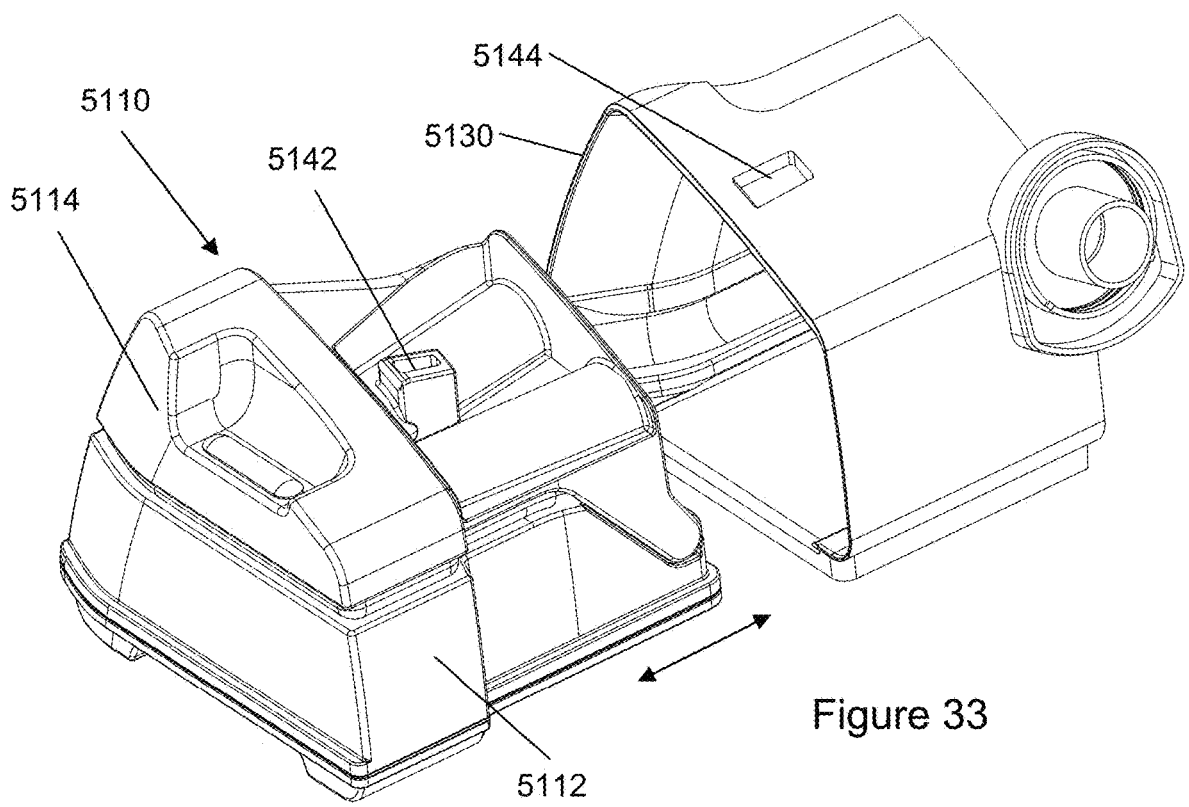

FIGS. 32-33 show the humidifier dock 5130 and the humidifier reservoir 5110, and in particular show the interaction between the lid protrusion 5142 and the dock locking recess 5144 according to one aspect of the present technology.

Figure 34:
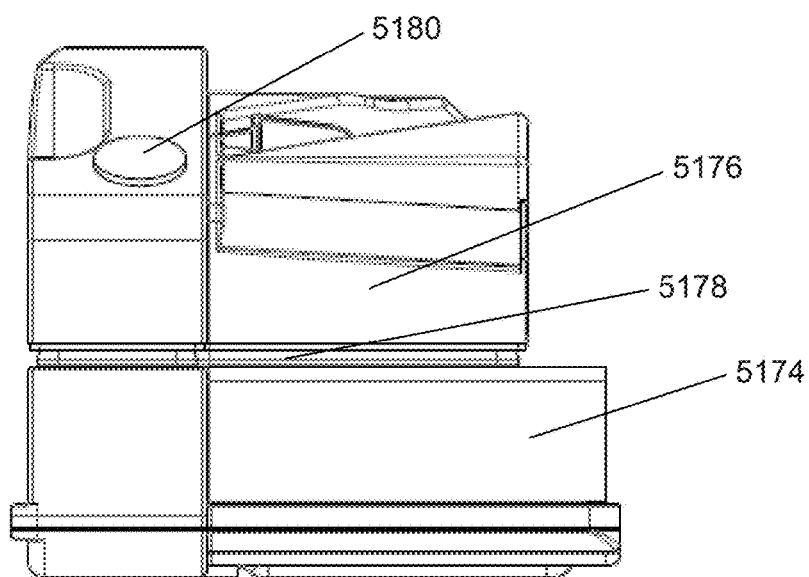

FIG. 34 show an example of the humidifier reservoir 5110 according to another example of the current technology, wherein it is configured with a re-filling cap 5180 and a base, top and variable portion may be affixed together.

FIGS. 35-38 shows other representations of a humidifier reservoir 5110 according to an aspect of the present technology, with particular regard to the arrangement of the inlet tube 5124 and the outlet tube 5126.

Figure 39:
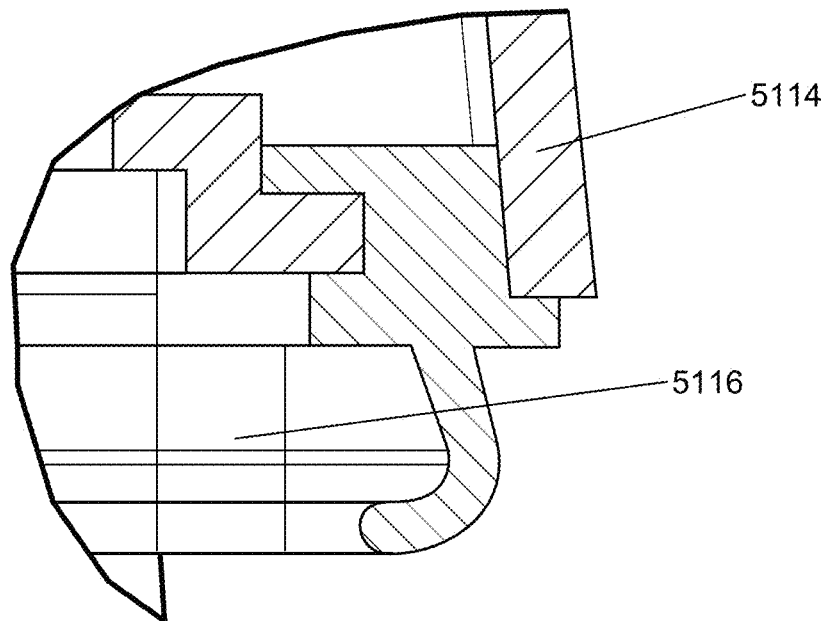

FIG. 39 shows a cross-sectional view of a reservoir lid 5114 and a variable portion in the form of a seal 5116 according to an aspect of the present technology.

Figure 40:
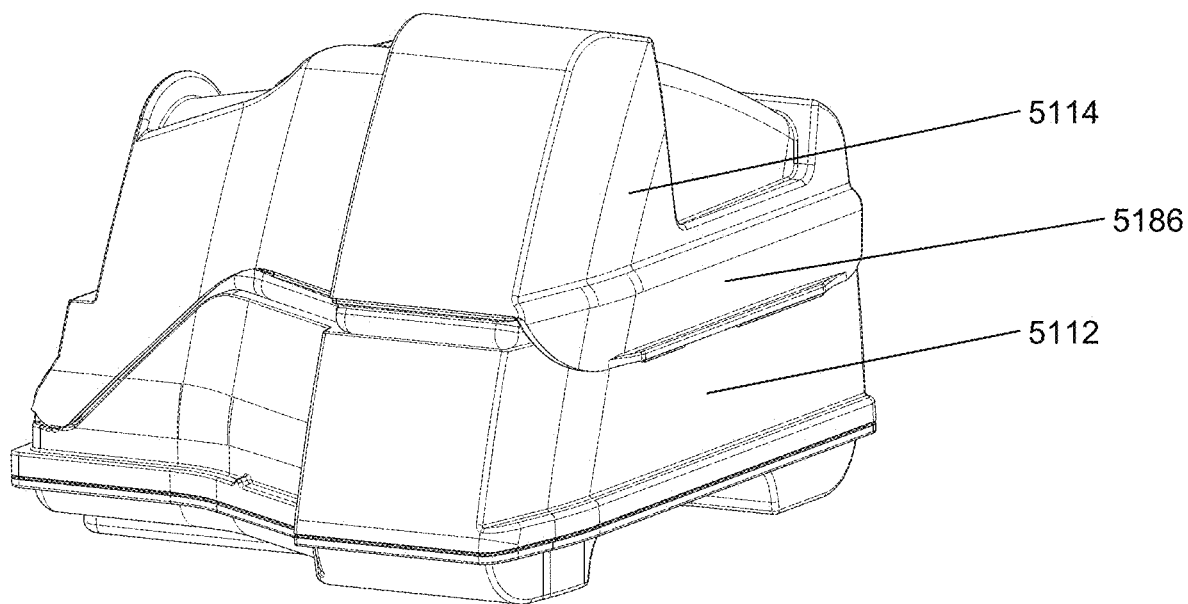

FIG. 40 shows an example of the humidifier reservoir 5110 according to another example of the present technology, wherein it is configured with a latch 5186.

5 DETAILED DESCRIPTION OF THE INVENTION

Before the present technology is described in further detail, it is to be understood that the technology is not limited to the particular examples described herein, which may vary. It is also to be understood that the terminology used in this disclosure is for the purpose of describing only the particular examples discussed herein, and is not intended to be limiting.

5.1 Treatment Systems

In one form, the present technology comprises apparatus for treating a respiratory disorder. Preferably the apparatus comprises a flow generator or blower for supplying pressurised respiratory gas, such as air, to the patient 1000 via an air delivery tube leading to a patient interface 3000.

5.2 Therapy

In one form, the present technology comprises a method for treating a respiratory disorder comprising the step of applying positive pressure to the entrance of the airways of a patient 1000.

5.2.1 Nasal CPAP for OSA

In one form, the present technology comprises a method of treating Obstructive Sleep Apnea in a patient by applying nasal continuous positive airway pressure to the patient.

5.3 Patient Interface 3000

A non-invasive patient interface 3000 in accordance with one aspect of the present technology comprises the following functional aspects a seal-forming structure 3100, a plenum chamber 3200, a positioning and stabilising structure 3300 and a connection port 3600 for connection to an air circuit 4170. In some forms a functional aspect may be provided by one or more physical components. In some forms, one physical component may provide one or more functional aspects. In use the seal-forming structure 3100 is arranged to surround an entrance to the airways of the patient so as to facilitate the supply of air at positive pressure to the airways.

5.4 Pap Device 4000

A preferred PAP device 4000 in accordance with one aspect of the present technology comprises mechanical and pneumatic components 4100, electrical components 4200 and is programmed to execute one or more algorithms 4300. FIG. 7 shows a prior art embodiment of a PAP device 4000, which is connectable to a humidifier 5000. The PAP device may also be integrated with a humidifier 5000 so that an external housing 4010 encases the components that perform the equivalent function of a PAP device 4000 as well as components that perform the equivalent function of a humidifier 5000.

FIG. 8 shows an example embodiment of such an integrated device comprising a PAP device 4000 and a humidifier 5000. It should be understood that subsequent references to a humidifier 5000 refers to the integrated device, in particular the components that perform the equivalent function of a humidifier 5000.

5.5 Humidifier 5000

5.5.1 Humidifier Overview

In one form of the present technology there is provided a humidifier 5000 comprising a water reservoir 5110, a heater plate 5120 and a water reservoir dock 5130.

5.5.2 Humidifier Mechanical Components 5100

5.5.2.1 Water Reservoir Dock 5130

Figure 13:
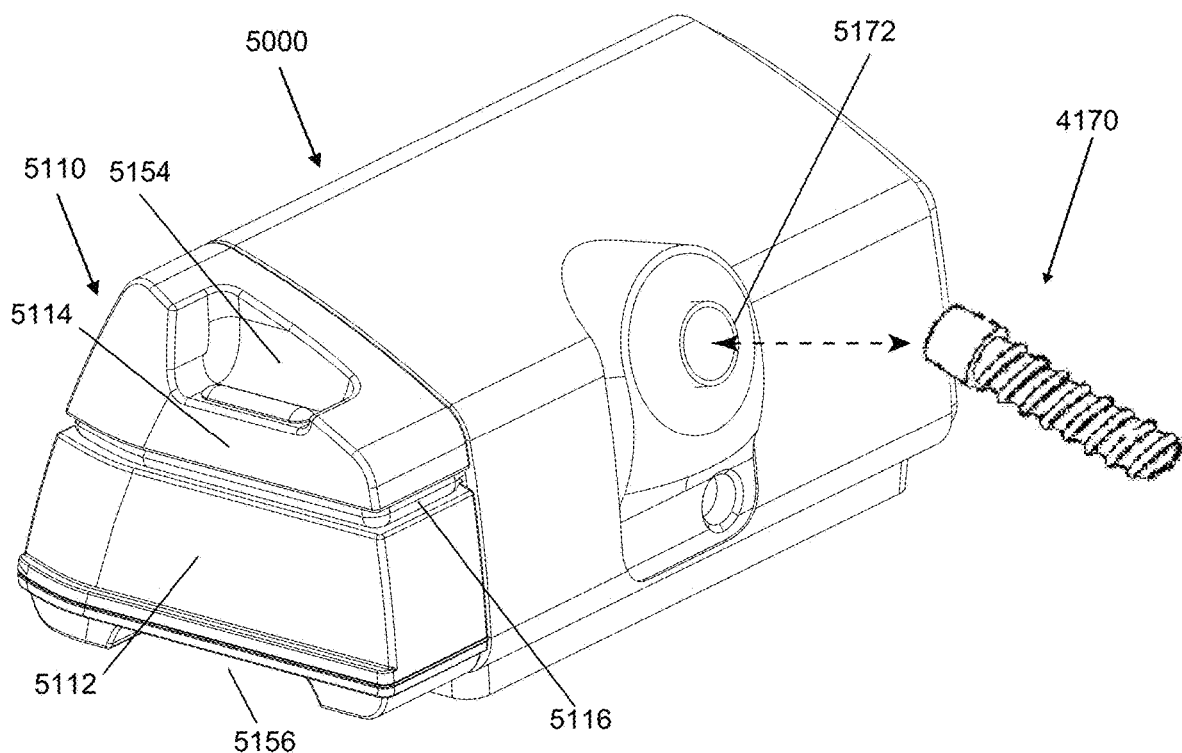
Figure 14:
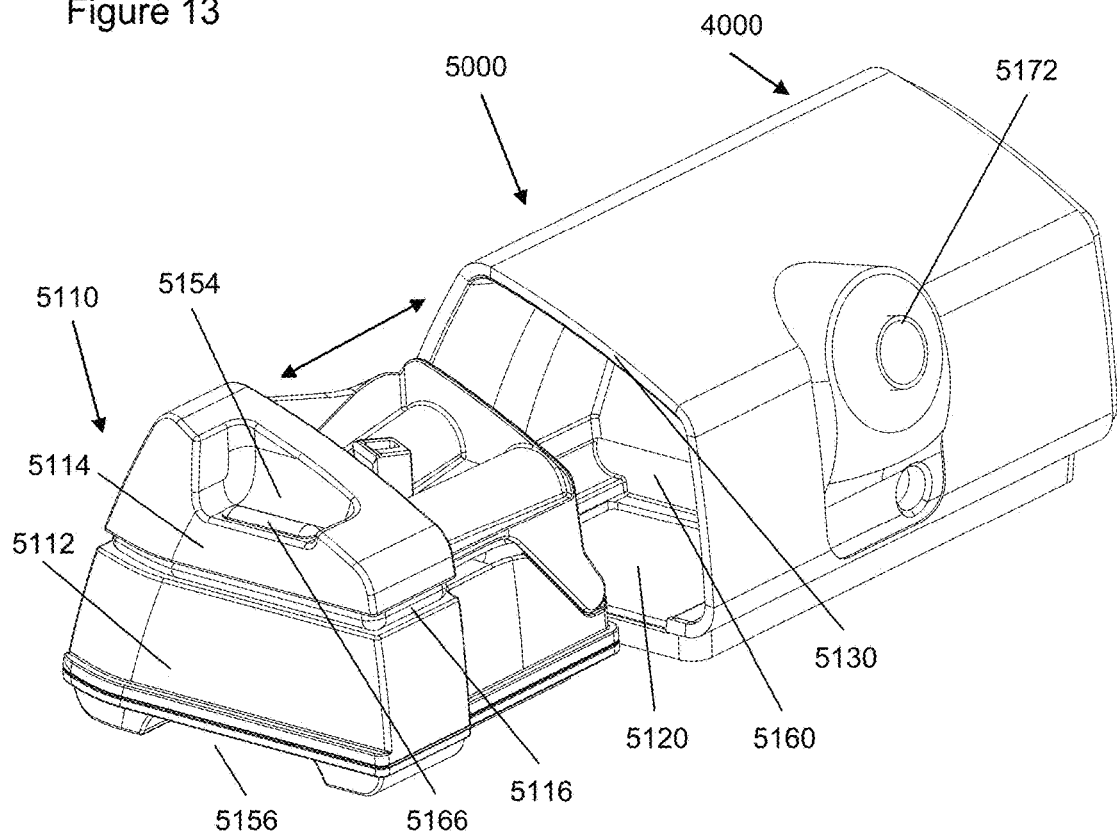

A water reservoir dock 5130 may be integrated with the humidifier 5000 as shown in FIG. 13-16. In this arrangement, the reservoir dock 5130 comprises a breathable gas outlet 5168 to output a flow of breathable gases to a water reservoir 5110, a humidified breathable gas inlet 5170 to receive the flow of breathable gases that has been humidified in the water reservoir 5110, and an air delivery conduit outlet 5172 to transfer the flow of humidified breathable gases to the air delivery conduit 4170. As shown in FIG. 14, the water reservoir dock 5130 may form a cavity 5160 to receive the water reservoir 5110. The cavity 5160 may include a top portion configured to cover at least a portion of the lid of the reservoir 5110 and a bottom portion including the heater plate 5020.

It should be understood that the reservoir dock 5130 may be provided separately to a humidifier 5000 in an alternate arrangement. In such an arrangement, additional interfaces may be used to connect the reservoir dock 5130 to the humidifier 5000.

In another arrangement, a water reservoir dock 5130 may comprise an opening in a substantially horizontal plane, so that the water reservoir 5110 may be inserted from above or below the water reservoir dock 5130.

5.5.2.2 Water Reservoir 5110

FIG. 9-12 show an example of a water reservoir 5110 according to the technology, which comprises a reservoir base 5112, a reservoir lid 5114, and a variable portion 5116. As shown in this example arrangement the variable portion 5116 may also function as a seal between the base 5112 and the reservoir lid 5114. The reservoir forms a cavity formed by a plurality of walls to hold a volume of liquid or water. The cavity of the reservoir 5110 is configured so that it is able to hold a given, maximum volume of liquid or water, typically several hundred millilitres, for example 300 millilitres (ml), 325 ml, 350 ml or 400 ml, although it is to be understood that other volumes of liquid may be utilised such as 100 ml, 200 ml, 250 ml, 500 ml or more or less.

The lid 5114 may comprise an inlet 5118 and an outlet 5122. The inlet 5118 comprises an inlet tube 5124 and the outlet 5122 comprises an outlet tube 5126. The lid 5114 may be pivotably connected to the base 5112 by hinges 5158 in such a way that it is able to be moved between an open position, as shown in FIG. 11, and a closed position, as shown in FIG. 9 and FIG. 10. When the water reservoir 5110 is in its closed configuration, the variable portion 5116 is put into sealing engagement between the base 5112 and the lid 5114.

The variable portion 5116 may be provided as part of the reservoir lid 5114 or as part of the reservoir base 5112, or independently of both. The variable portion 5116 may be engaged with the reservoir lid 5114 or the reservoir base 5112 by any number of means including, and not limited to, ultrasonic welding, friction fitting, gluing or by using an intermediate component. The variable portion 5116 may comprise a carrier 5117 (as shown in FIG. 12).

In an arrangement, the variable portion 5116 may not be directly engaged with the base 5112 or lid 5114 but coupled to one or both of the lid 5114 and the base 5112 such that each of the base 5112 and the lid 5114 may be formed as two separate parts that are able to be assembled with the variable portion 5116 coupled therebetween. Alternatively the variable portion 5116 may be coupled to either the lid 5114 or the base 5112.

In an alternative arrangement the variable portion 5116 may be located within a wall of the reservoir base 5112 and/or a wall of the reservoir lid 5114 rather than being on the edge of either the reservoir base 5112 or the reservoir lid 5114. Thus, in such an arrangement the variable portion would not be between the reservoir base 5112 and the reservoir lid 5114 but within the reservoir base 5112 and/or the reservoir lid 5114. There may be more than one variable portion 5116 to provide more compliance in movement of the reservoir 5110.

The reservoir base 5112 comprises a conducting portion that is configured to couple with a heater plate 5130 of the humidifier to allow thermal engagement and thermal transfer of heat to the liquid or water within the base. The base may comprise a base upper body 5146, a base bottom plate 5148, and a conducting portion in the form of a base conductor plate 5152, as shown in FIG. 12. All or a part of the base conductor plate 5152 may be made of a different material (e.g. aluminium or another heat conducting metal) than the base upper body 5146 and/or the base bottom plate 5148, which may be made of a plastic or thermoplastic polymer, for example, a polycarbonate material. The base conductor plate 5152 may comprise of a sealing element 5150, which may be integrated to, and/or sealingly connected to both the base upper body 5146 and the base bottom plate 5148 to prevent egress of water from the water reservoir 5110 through its bottom.

It should be appreciated that the reservoir base 5112 may be constructed in any number of parts. The reservoir base 5112 may be constructed as a single part made of, for example, aluminium or another heat conducting metal. In another arrangement, the reservoir base 5112 may be constructed in multiple parts such as two parts comprising a lower component and an upper component. The lower component may include: a reservoir base conductor plate 5152, sealing element 5150 and base bottom plate 5148. The base bottom plate is constructed at least in part from a heat conducting material, for example, aluminium or another heat conducting metal. The upper component may include a base upper body 5146 constructed from, for example, a polycarbonate material. The upper and lower components may be sub-divided to form further arrangements consisting of greater number of parts, for example the sealing element 5150 may be a separate component.

Water Reservoir-to-Humidifier Connection

When in use, the water reservoir 5110 is removably coupled with the humidifier 5000 as shown in FIG. 13-16 by inserting the water reservoir into the water reservoir dock 5130, for example by sliding, so that the inlet 5118 of the water reservoir 5110 is configured to receive the flow of breathable air that is output by the PAP device 4000, and to direct the flow of breathable air into the water reservoir 5110. Moisture is added to the flow of breathable air as the breathable air travels through the reservoir 5110, and the humidified flow of breathable air exits the reservoir 5110 through the outlet tube 5126 and to the reservoir outlet 5122. The reservoir outlet 5122 is connectable to an air delivery circuit or air delivery conduit 4170 to deliver the flow of humidified breathable air to the patient 1000.

Figure 16:
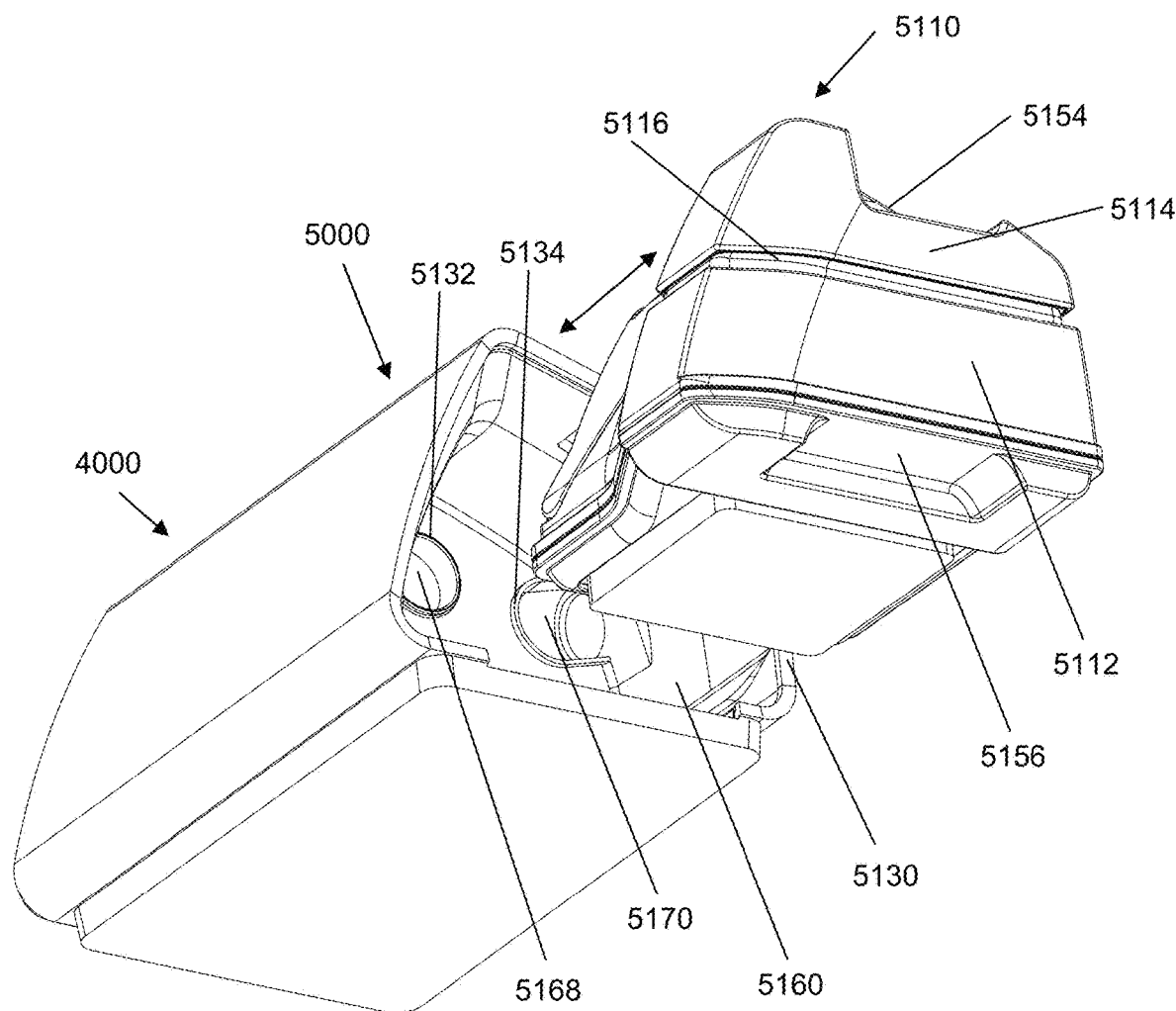

The double-ended arrows in FIG. 14 and FIG. 16 show the direction of relative motion, i.e. generally horizontal movement, between the humidifier 5000 and the water reservoir 5110 in connecting and disconnection with each other in this arrangement. However, it is noted that the water reservoir 5110 may be coupled to the humidifier 5000 by other means such as being inserted into the humidifier in a generally vertical direction. In the illustrated arrangement the reservoir outlet 5122 is connected to the reservoir dock outlet 5168, through which the humidified flow of breathable air travels to the humidifier outlet 5172. The humidifier outlet 5172 is connectable to the air delivery circuit or air delivery conduit 4170 as indicated in FIG. 13 by the double-ended arrow. One feature of such an arrangement is that the humidifier reservoir 5110 must be removed from the reservoir dock 5130 to fill the humidifier reservoir 5110 with water. This arrangement may reduce the likelihood of the user over-filling the water reservoir 5110 over the given, maximum volume of liquid or water, as the humidifier reservoir 5110 incorporates means to prevent over-filling when the lid 5114 is in its open position as described further below.

As shown in FIG. 16, first and second dock seals 5132, 5134 may be provided to seal the connection between the reservoir inlet 5118 and the dock 5130 and the connection between the reservoir outlet 5122 and the dock 5130.

Reservoir Handles

FIG. 13-16 show an upper handle 5154 that is located on the reservoir lid 5114, and a lower handle 5156 that is located on the reservoir base 5112. These handles are intended to assist the patient 1000 to grip and hold the water reservoir 5110. In the shown arrangement, the handles 5154 5156 are located away from the hinges 5158 such that by holding the reservoir 5110 by the handles 5154 5156 the patient 1000 imparts forces onto the reservoir 5110 compressing the variable portion 5116, which pushes the lid 5114 and the base 5112 towards each other. This compression force may also help maintain the variable portion 5116 in sealing engagement between the reservoir base 5112 and the reservoir lid 5114. It is to be understood that the handles 5154 and 5156 may be placed on other components or areas of the water reservoir 5110. A friction grip 5166 may be provided on a surface of either or both of the handles 5154 5156 as shown in FIG. 14. The friction grip 5166 may be constructed from a higher friction material than the primary material used to construct the water reservoir 5110. For example, the friction grip 5166 may be constructed from an elastomeric material such as silicone whereas the water reservoir 5110 may primarily be constructed from a polycarbonate material.

Reservoir Variable Portion

In the illustrated arrangement, when the water reservoir 5110 is in use, the variable portion 5116 is maintained in sealing engagement between the reservoir base 5112 and the reservoir lid 5114. However, as mentioned above the variable portion 5116 may alternatively be formed as part of the reservoir base 5112 and/or the reservoir lid 5114 and not form a seal between the reservoir base 5112 and the reservoir lid 5114. The variable portion 5116 may be constructed from an elastomeric material such as silicone, TPE, TPE polyester, TPE polyurethane or natural rubber. In choosing the material to be used for the variable portion 5116 it may be advantageous to choose one that does not experience mechanical relaxation across the range of storage and operational temperatures that the variable portion 5116 may be exposed to. One example of a material for the variable portion 5116 which meets these requirements may be silicone.

Figure 15:
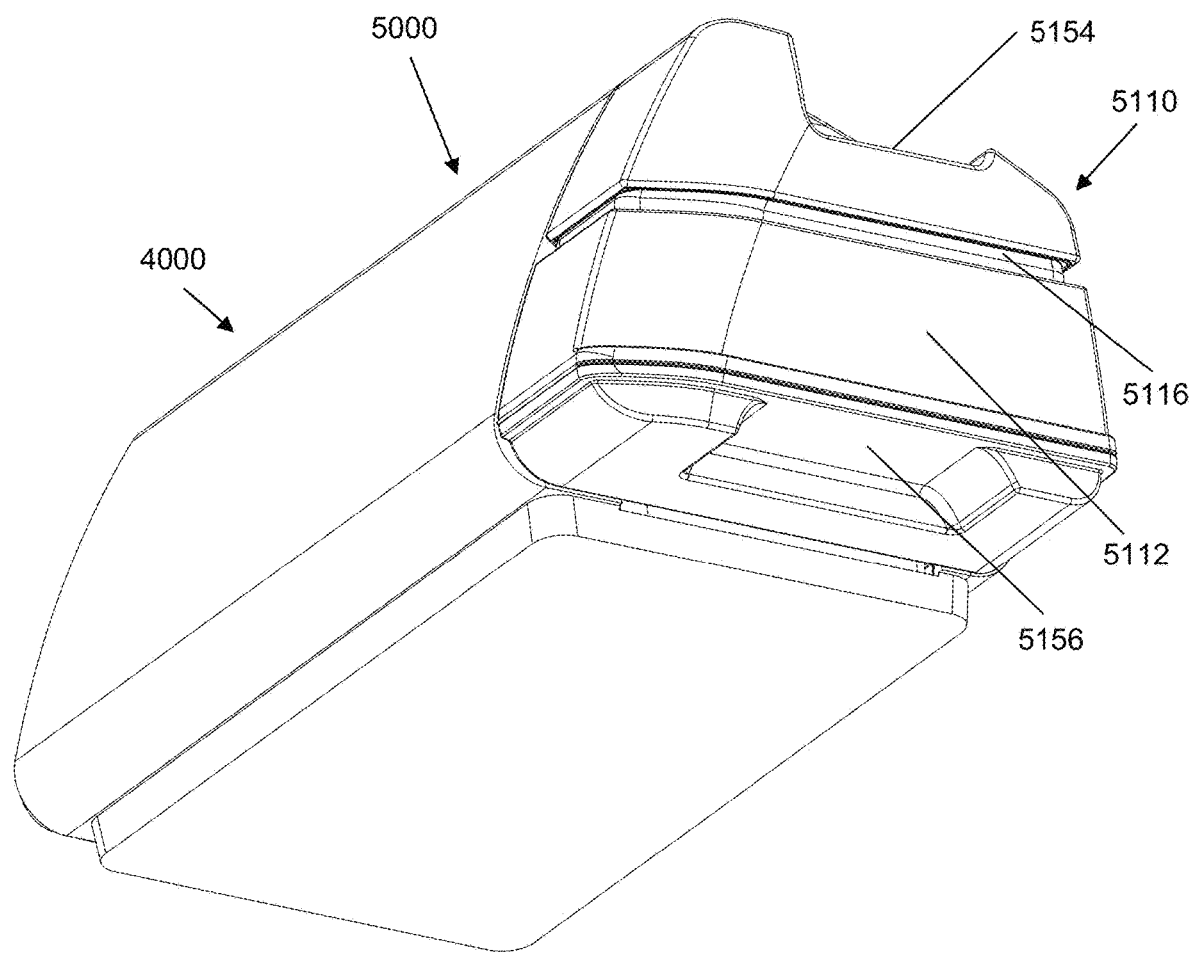

In the arrangement shown in FIG. 15-16, the water reservoir 5110 is connected with the humidifier 5000 by placing the water reservoir 5110 in the water reservoir dock 5130. In this arrangement, the heights and shapes of the dock internal cavity 5160 and the water reservoir 5110 are such that when the water reservoir 5110 is engaged with the water reservoir dock 5130 the variable portion 5116 is compressed, for example by between about 1 mm and about 5 mm, for example by about 2 mm, about 3 mm or about 4 mm. Thus, the shape of the portion of the water reservoir 5110 that is inserted into the dock 5130 is complementary to the shape of the dock cavity 5160 and the height of the water reservoir 5110 when variable portion 5116 is compressed is slightly less than the height of the dock cavity 5160 to enable the insertion of the water reservoir 5110 into the dock cavity 5160. The variable portion 5116 may be constructed with a cross-section shape such as one shown in FIG. 39. A compressive force is required to sufficiently compress the variable portion to allow relative movement, such as sliding between the water reservoir 5110 and the water reservoir dock 5130. For example a compression force as measured at the handle recesses 5154, 5156 of between about 10 N and about 30 N, or about 20 N, or some other compression force as required to allow insertion of the water reservoir 5110 into the dock cavity 5160. The vertical gap achieved between the water reservoir 5110 and the dock internal cavity 5160 may be between about 1 mm and about 5 mm, for example about 2 mm, 3 mm or 4 mm, when the compressive force is applied at the handle recesses and the water reservoir 5110 is connected with the reservoir dock 5130. The water reservoir 5110 and the reservoir dock 5130 may be arranged so that the amount of compression in the variable portion 5116 is reduced once the water reservoir 5110 is connected with the reservoir dock 5130 and the patient 1000 is no longer applying a compressive force. The reduction in compression may be between about 0.5 mm and about 2.5 mm, for example about 1 mm, 1.5 mm or 2 mm.

A reservoir latch 5186 may be provided on the water reservoir 5110, as shown in FIG. 39, so that when the reservoir latch 5186 is engaged, it secures the reservoir lid 5114 and reservoir base 5112 together to prevent the reservoir lid 5114 and the reservoir base 5112 from separating and maintains the variable portion 5116 in a compressed state. The latch may also maintain the variable portion 5116 in sealing engagement between the lid 5114 and the base 5112 when the variable portion 5116 is located between the lid 5114 and the base 5112. The latch 5186 may be configured to allow further compression of the variable portion 5116. This would allow insertion of the water reservoir 5110 into the reservoir dock 5130 in the manner described above, and for the variable portion 5116 to retain its advantageous properties regarding improvements to thermal engagement as described below.

In an alternative arrangement, not shown, the water reservoir 5110, may be inserted into the dock cavity 5160 from a vertical direction rather than using a sliding motion. In such an arrangement the dock cavity of the humidifier 5000 may comprise a moveable cover portion, such as a lid or top portion, that is at least partially opened to allow insertion of the water reservoir 5110 and closed following insertion to secure the water reservoir 5110 within the dock cavity 5160.

Air Flow Path

FIG. 17-19 show an exemplary path of the flow of breathable air through the reservoir 5110 as it enters through the inlet 5118 and exits through the outlet 5122. The figures are arranged chronologically in three distinct orthogonal views per figure to demonstrate the exemplary flow path visually. In this arrangement the flow of breathable air received through the inlet 5118 passes through the inlet tube 5124 (FIG. 17), into the internal volume of the water reservoir 5110 (FIG. 18), and then passes through the outlet tube 5126 to exit the water reservoir 5110 at the outlet 5122 (FIG. 19) as humidified breathable air. FIG. 17-19 show the reservoir 5110 with the lid 5114 and the base 5112 in exploded view orientation for clarity, and any flow of the air that occurs in the internal volume of the reservoir 5110 is shown in dotted lines, and the direction of the arrows shown indicate the general direction of the exemplary flow of breathable air. Although it is noted that the nature of gas or air flow may involve the swirling of air rather than a straight and direct air flow path.

The path of the flow of breathable air demonstrated in FIG. 17-19 is exemplary only, and is aimed to demonstrate one of many paths that the flow of breathable air may traverse through, namely that it enters the water reservoir 5110 through the inlet 5118 and exits through the outlet 5122 after experiencing some degree of swirling within the volume of the water reservoir 5110. A person skilled in the art would understand that the particles or molecules that form the flow of breathable air may not follow a single path within the water reservoir 5110 due to a number of factors, including, for example, localised turbulence (eddies) or pressure gradients within the water reservoir 5110. As a result the cumulative path of the flow of breathable air may comprise any number of paths wherein it experiences various degrees of 'swirling' within the water reservoir 5110 prior to exiting via the outlet tube 5126 at the outlet 5122. It is also possible that some small portion of the flow of breathable air may escape the water reservoir 5110 as a leak.

Thermal Contact/Engagement

One aspect of this technology is improved thermal contact or engagement between the base 5112 of the water reservoir and the heater plate 5120 of the humidifier. The improved thermal contact or engagement may be facilitated by the supply of pressurized gas to the humidifier reservoir 5110 from a PAP device.

In one arrangement, the water reservoir 5110 may be configured so that when it is placed in the water reservoir dock 5130 the reaction to the compression of the variable portion 5116, i.e. a force attempting to expand the variable portion 5116, pushes the base 5112 of the water reservoir 5110 against the heater plate 5120 to improve the level of thermal engagement between the heater plate 5120 and the base 5112. This occurs as a result of the variable portion 5116 initially being compressed when it is inserted into the reservoir dock 5130 as described above, and then the compression is released or reduced allowing the variable portion 5116 to expand towards its relaxed or uncompressed state. Thus, the variable portion 5116 is acting like a spring that may be biased to push the reservoir base 5112 and/or the reservoir lid 5114 in a direction perpendicular to the heater plate 5120 until the variable portion 5116 is in a reduced compressed state. As the reservoir 5110 is confined within the reservoir dock 5130 or by some other means the level of compression of the variable portion 5116 is transferred as a force that encourages improved thermal engagement with the heater plate 5020. FIG. 20 illustrates this effect by indicating the distributed forces or pressures that are applied to the lid 5114, variable portion 5116 and the base 5112 by the arrows shown.

The force required for compression of the variable portion 5116 when the water reservoir 5110 is connected with the humidifier 5000 is primarily in the direction tangential to the pivoted opening direction of the water reservoir 5110, which may be the same direction as the normal to a surface of the conductive portion, and is reacted by the water reservoir dock 5130 at its contacting points and/or surfaces, thereby pushing the base 5112 of the water reservoir 5110 and the heater plate 5120 together. As a corollary, a decrease of the compression resulting in an increase in height of the variable portion 5116 will reduce the force between the base 5112 and the heater plate 5120. In other words, varying the height of the variable portion in the reservoir varies a level of thermal engagement between the conductive portion and the heater plate.

The water reservoir 5110 may be configured so that the direction of thermal engagement with the heater plate 5120 is in the same direction as the normal direction of a surface of the conductive portion.

The magnitude of this force may be between about 5 N and about 15 N when measured at the heater plate 5120 when the water reservoir 5110 is placed in the water reservoir dock 5130. However, it should be understood that different configurations of the water reservoir 5110 may require different magnitudes of compression force. The magnitude of this force may be altered by modifying the design of any or all of the seal 5116, the lid 5114, the base 5112, or the reservoir dock 5130. For instance if the variable portion 5116 was constructed of a material with higher Young's modulus, it would correspondingly increase the magnitude of the force. It should be noted that FIG. 20 only shows forces and pressures in the vertical direction.

Furthermore, when the water reservoir 5110 is connected with the humidifier 5000, the pressurized flow of breathable air received from the PAP device pressurizes the interior of the reservoir 5110 and may further encourage an expansion of the variable portion 5116 that pushes the base 5112 of the water reservoir 5110 against the heater plate 5120 to improve the level of thermal engagement, or the level of thermal contact, between the heater plate 5120 and the base 5112. FIG. 21 illustrates this effect by indicating the distributed forces or pressures that are applied to the lid 5114 and the base 5112 by the arrows shown. The presence of above-atmospheric pressure within the water reservoir 5110 is shown to result in forces in the direction of thermal engagement, and is reacted by the water reservoir dock 5130 at its contacting surfaces, thereby pushing the base 5112 of the water reservoir 5110 and the heater plate 5120 towards each other in the direction of thermal engagement. The magnitude of this force may be between about 5 N and about 15 N when measured at the heater plate 5120 at 20 cm $H_2O$ of pressure. However, it should be understood that different configurations of the water reservoir 5110 may require different magnitudes of force, which may be achieved by varying the surface area that the pressure acts on, or the effective pressure that acts on the surface. Such changes may be achieved, for example, by a pressure regulating valve. It should be noted that FIG. 21 only shows forces and pressures in the vertical direction, as the thermal engagement occurs in the vertical direction. Thus, the variable portion in the reservoir 5110 enables movement of the reservoir base 5112 and/or the reservoir lid 5114 in response to an increase in pressure above atmospheric pressure in the reservoir 5110 to improve thermal engagement of the reservoir base 5112 with the heater plate 5020. It is envisaged that, in another arrangement, substantially the same effects as those described above may be achieved with a non-opening variable portion of a water reservoir 5110. The water reservoir 5110 and the reservoir dock 5130 may be substantially arranged so that elasticity or flexibility is provided by an elastomeric material or a joint that allows freedom of movement (e.g. a sliding connection, or a concertina section of pliable plastic or a flexible portion in the water reservoir) in the direction of the heat transfer. In this configuration the lid 5114 and the base 5112 may be unconstrained relative to each other in the direction of thermal contact The reservoir 5110 may then be constrained in the direction of the heat transfer in another manner (e.g. by a water reservoir dock or a similar housing) to create a force that reacts to balance the pressure created in the interior of the reservoir 5110 by the pressurized flow of breathable air, wherein some of the reaction force may occur at the heater plate 5120 to improve thermal contact. In such arrangements, another opening to re-fill the water reservoir 5110 may be introduced on the reservoir 5110, such as on the lid 5114, and it may comprise a separate seal. Such an opening may be configurable between an open and a closed position, for example, by a cap or a refilling lid. FIG. 34 shows an example of such an arrangement, including a base 5174, a top 5176, a variable portion 5178 and a re-filling cap 5180. The base, the top and the variable portion may be affixed together in this arrangement, and in such a case re-filling of the reservoir would be accommodated by the re-filling cap, 5180. The re-filling cap 5180 may be placed such that when the humidifier reservoir 5110 is engaged with the reservoir dock 5130 the re-filling cap 5180 is not accessible. Such an arrangement may preserve the advantage described above, namely that the reservoir 5110 is not able to be re-filled while it is engaged with the reservoir dock 5130. Furthermore, the variable portion 5178 may be replaced by any mechanism known in the art that is able to accommodate a change in vertical length within a reservoir.

In a yet another alternate arrangement, the pressurized flow of breathable air may be used to improve the level of thermal contact between the humidifier reservoir 5110 and the heater plate 5120 by pressurisation or inflation of a chamber, body or surface that acts on the humidifier reservoir 5110, which in turn may push the water reservoir 5110 and the heater plate 5120 together in the direction of thermal engagement. Similarly the supply of the pressurized flow of breathable air may pressurize or inflate a chamber, body or surface that acts upon the heater plate to push the heater plate 5120 and water reservoir 5110 together in the direction of thermal engagement.

The chamber may be arranged on the outside of the reservoir and communicated with the flow of breathable gas. A surface of the chamber may be connected with the reservoir in the direction of thermal engagement so that varying the pressure of the flow of breathable gas in the reservoir varies the size of the chamber and changes a level of thermal engagement between the conductive portion and the heater plate. The chamber being arranged to push the reservoir towards the heater plate 5020 and/or the heater plate 5020 towards the reservoir when the size of the chamber increases.

In an alternate arrangement of the reservoir dock 5160, wherein the opening is substantially in the horizontal plane and thus the water reservoir 5110 is inserted from above or below the reservoir dock 5160 as described above, the water reservoir dock 5160 may include a retaining mechanism (for example, a lid that closes above the water reservoir 5110) to hold the water reservoir 5110 in its intended position. In such an arrangement, the reservoir dock lid may be configured to compress the variable portion 5116 which would in turn push the reservoir 5110 against the heater plate 5120. Similarly, the reservoir 5110 may be configured so that when the reservoir dock lid is closed, and the pressurized flow of breathable air pressurizes the interior of the reservoir 5110, it pushes the reservoir lid 5114 and the reservoir base 5112 apart that acts on the variable portion to try to expand or un-compress the variable portion, and in turn enhances the level of thermal contact between the reservoir base 5112 and the heater plate 5120.

The level of thermal contact may also be improved using a spring loaded or sprung heater plate as is known in the prior art. The heater plate may be constructed with a convex or domed shape towards the humidifier reservoir 5110 so that when the humidifier 5110 is engaged with the reservoir dock 5130 the convex heater plate is flattened, which generates a clamping force pushing the heater plate 5120 to the water reservoir 5110. Similarly, the conductor plate 5152 of the water reservoir 5110 may be domed or convex shaped and be configured to be flattened towards to the heater plate when the water reservoir 5110 is engaged in the dock cavity 5180 of the humidifier 5000.

Any one of the above means of improving thermal contact may be used independently of each other, or in any combination thereof, including in combination with any prior art means of achieving or improving thermal engagement between the humidifier reservoir and the heater plate.

Reservoir Inlet/Outlet

In one arrangement, the reservoir inlet 5118 and the reservoir outlet 5122 may be oriented horizontally and on the same surface, as shown in FIG. 12. The reservoir inlet 5118 includes an inlet tube 5124 that extends from the exterior of the reservoir into the interior volume of the reservoir to provide a flow path for the inlet flow of pressurized gas into the reservoir 5110. The reservoir outlet 5122 includes an outlet tube 5126 that extends from the interior of the reservoir 5110 to the exterior of reservoir 5110 to provide a flow path for the outlet flow of humidified pressurized gas from the reservoir 5110, as shown in FIG. 22.

Figure 22:
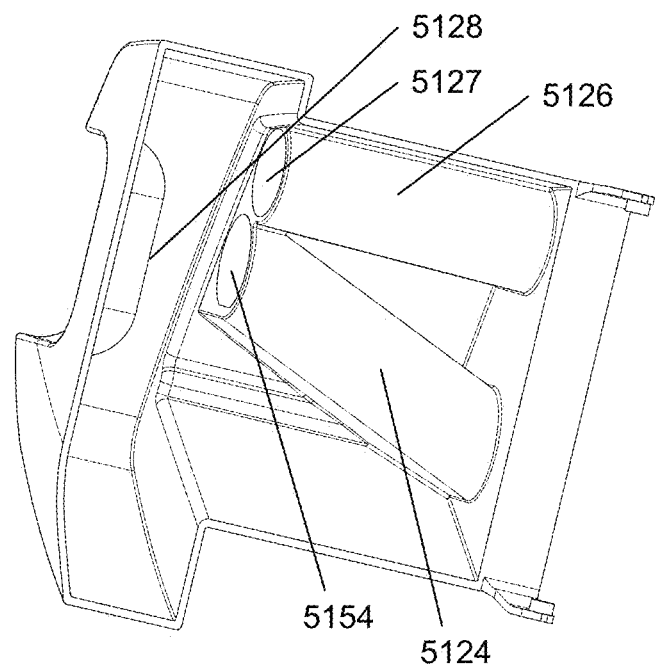
Figure 23:
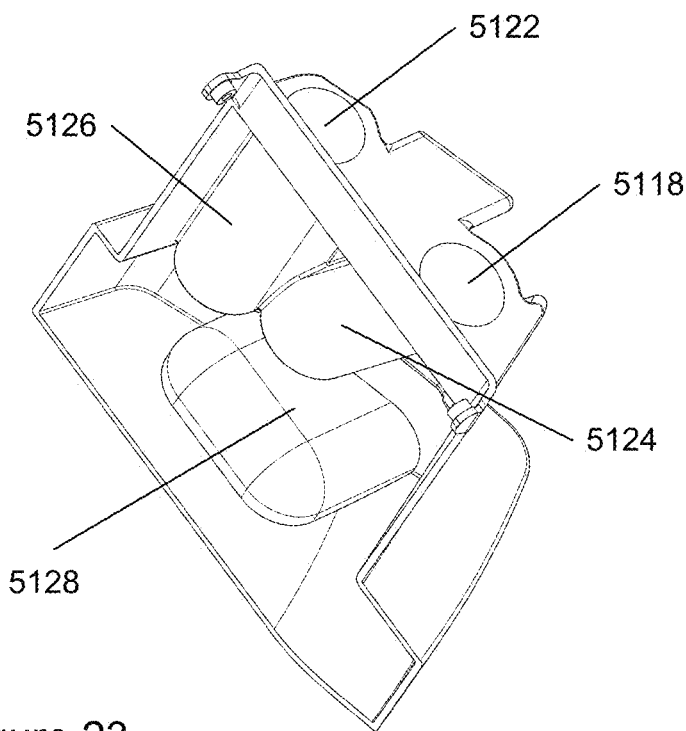
Figure 24:
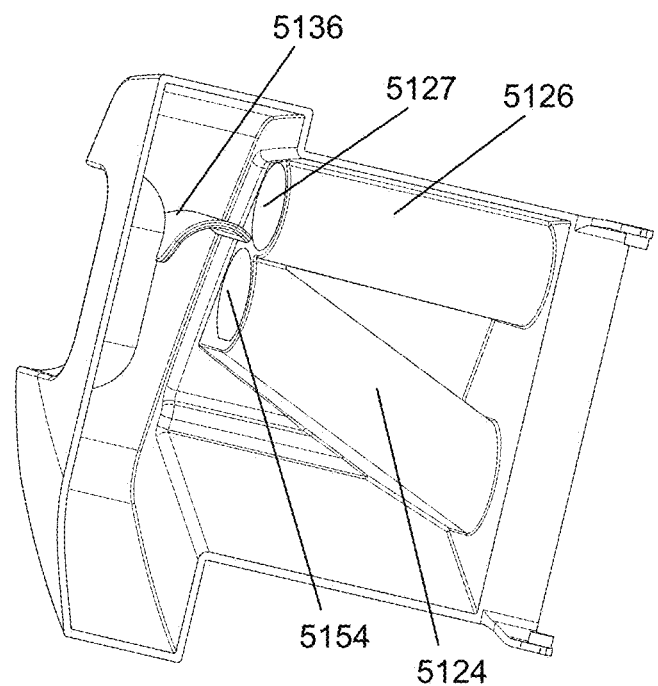
Figure 25:
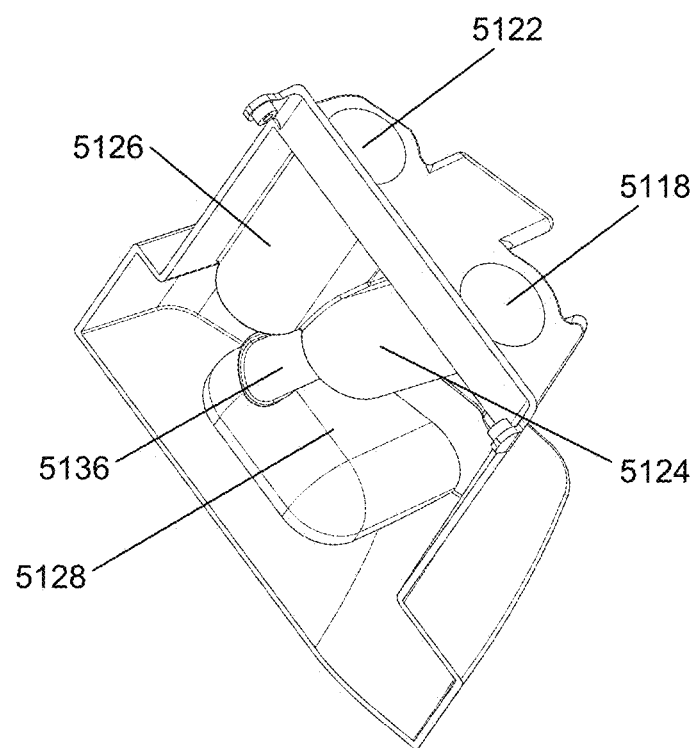
Figure 26:
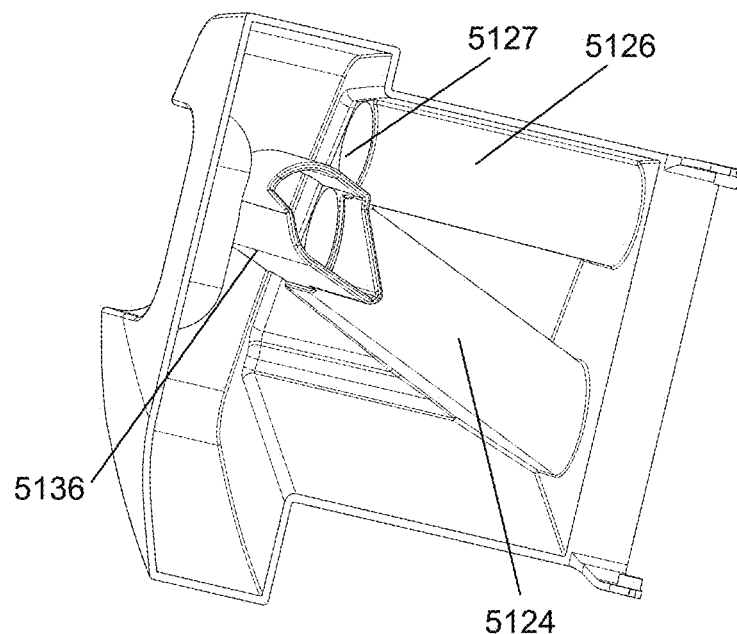
Figure 27:
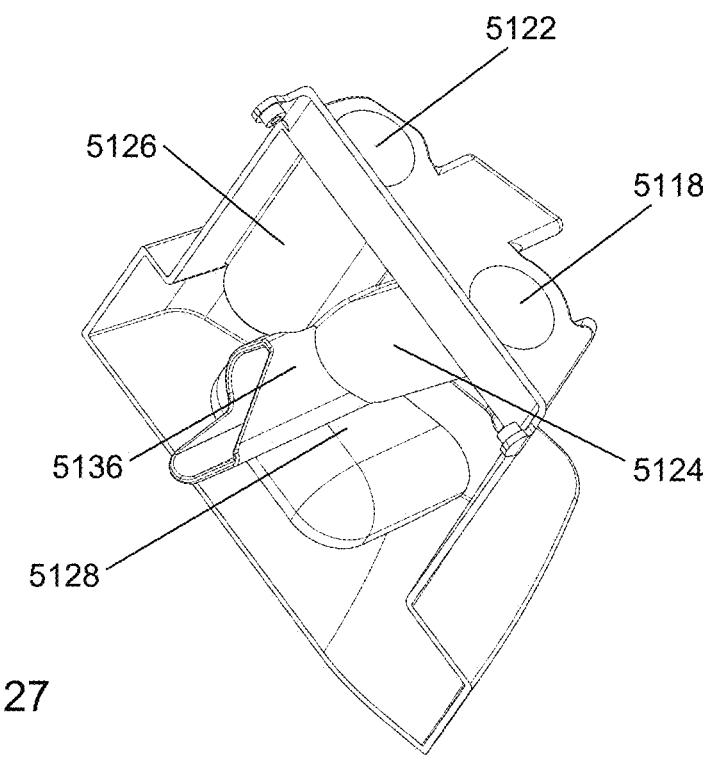

As shown in FIG. 22-23, the reservoir 5110 may include an end wall 5128 that is near and opposed to an interior end 5125 of the inlet tube 5124. The inlet tube 5124 directs the inlet airflow to the inner end wall 5128 of the reservoir 5110 thus directing the air to flow across the whole water surface before it reaches an interior end 5127 of the outlet tube 5126 and flows out of the outlet 5122 through the outlet tube 5126. FIG. 24-27 show examples of other arrangements, wherein the reservoir 5110 may include a turning vane 5136 which is placed near the interior end 5125 of the inlet tube 5124. The turning vane 5136 may be formed as an extension of the inlet tube 5124 as shown in FIG. 26-27, or the turning vane 5136 may be a separate component located adjacent to or coupled with the inlet tube 5124. The turning vane may also be profiled as shown in FIG. 26-27.

The water reservoir 5110 is preferably configured to provide tilt spillback protection from the water flowing back through the outlet tube 5126 or the inlet tube 5124. Water egress through the inlet tube 5124 is particularly undesirable as it may introduce water into the PAP device 4000 and may damage electronic components (such as an electric motor, a flow sensor or a printed circuit board) from exposure to water. In one arrangement the reservoir 5110 achieves spillback protection by arranging the inlet tube outlet 5125 so that when the reservoir 5110 is rotated by 90 degrees in any direction from its working, horizontal orientation the given maximum volume of water is able to be stored in the reservoir 5110 without reaching the inlet tube outlet 5125.

Figure 28:
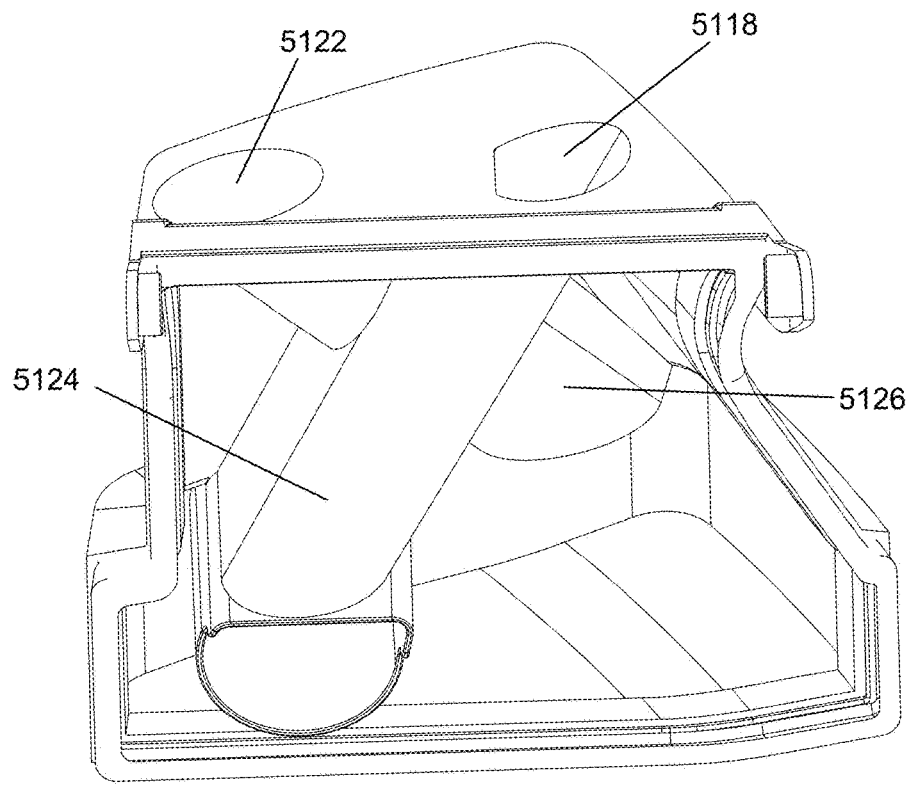
Figure 29:
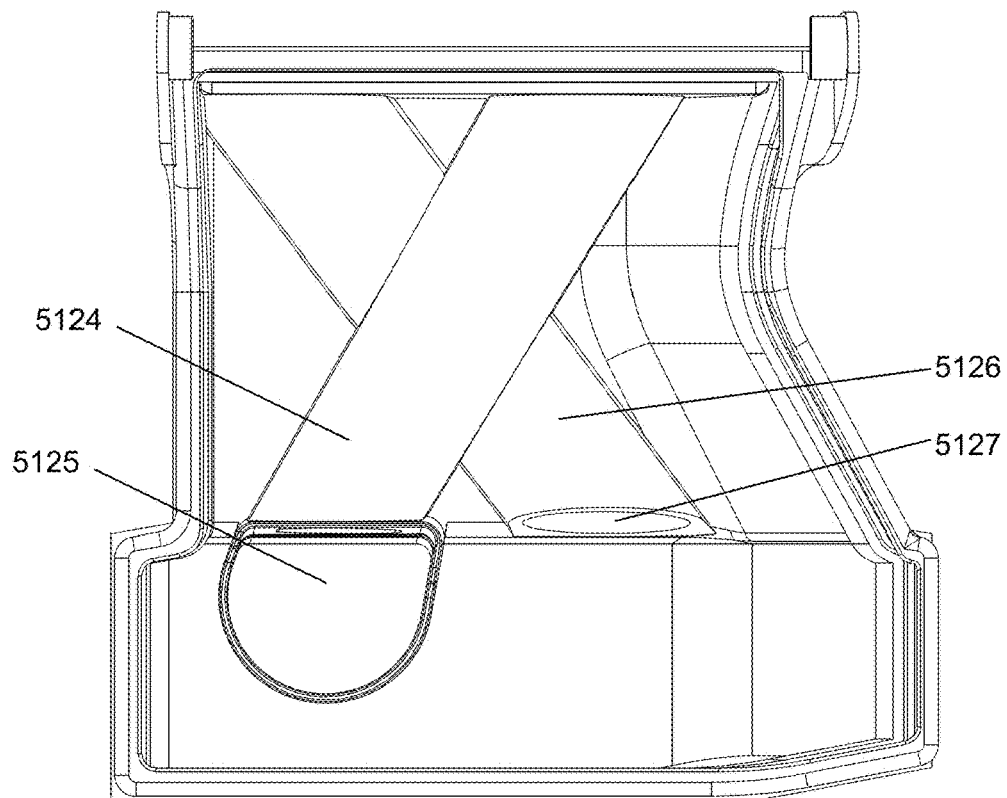

In another arrangement, the reservoir 5110, the axes of inlet tube 5124 and the outlet tube 5126 may intersect when viewed from above as shown in FIG. 28-29. The inlet tube 5124 and outlet tube 5126 are not connected to each other as one of the tubes passes below the other tube, such as the inlet tube 5124 passes below the outlet tube 5126.

This configuration may improve the tilt spillback protection by arranging the inlet tube 5124 and the outlet tube 5126 such that when the reservoir 5110 is tilted to its side (substantially about the axis of the inlet/outlet), and water reaches the lower of the interior end 5125 of the inlet tube 5124 or the interior end 5127 of the outlet tube 5126, the water must rise higher to exit the reservoir 5110 as shown in FIG. 29. In comparison, if the inlet tube 5124 and the outlet tube 5126 were parallel, when water reaches the lower of the interior end 5125 of the inlet 5124 or the interior end 5127 of the outlet tube 5126 it would then be able to freely flow out of the reservoir 5110 through the inlet tube 5124 or the outlet tube 5126.

One example of the above spillback prevention technology arranges the inlet tube 5124 and the outlet tube 5126 such that the axes defined by the interior end 5125 of the inlet 5124 and the exterior end 5190 of the outlet 5126 and the interior end 5127 of the outlet 5126 and the exterior end 5188 of the inlet 5124 are substantially parallel to each other.

Crossing the inlet tube 5124 and the outlet tube 5126 creates a geometric configuration wherein the water level must reach the higher of the inlet and outlet tube interior ends 5125, 5127 to be able to exit the reservoir 5110, or the water level must reach the lower of the inlet and outlet tube interior ends 5125, 5127 and extend along the entire length of the inlet tube 5124 or outlet tube 5126 to be able to exit the reservoir 5110.

Figure 35:
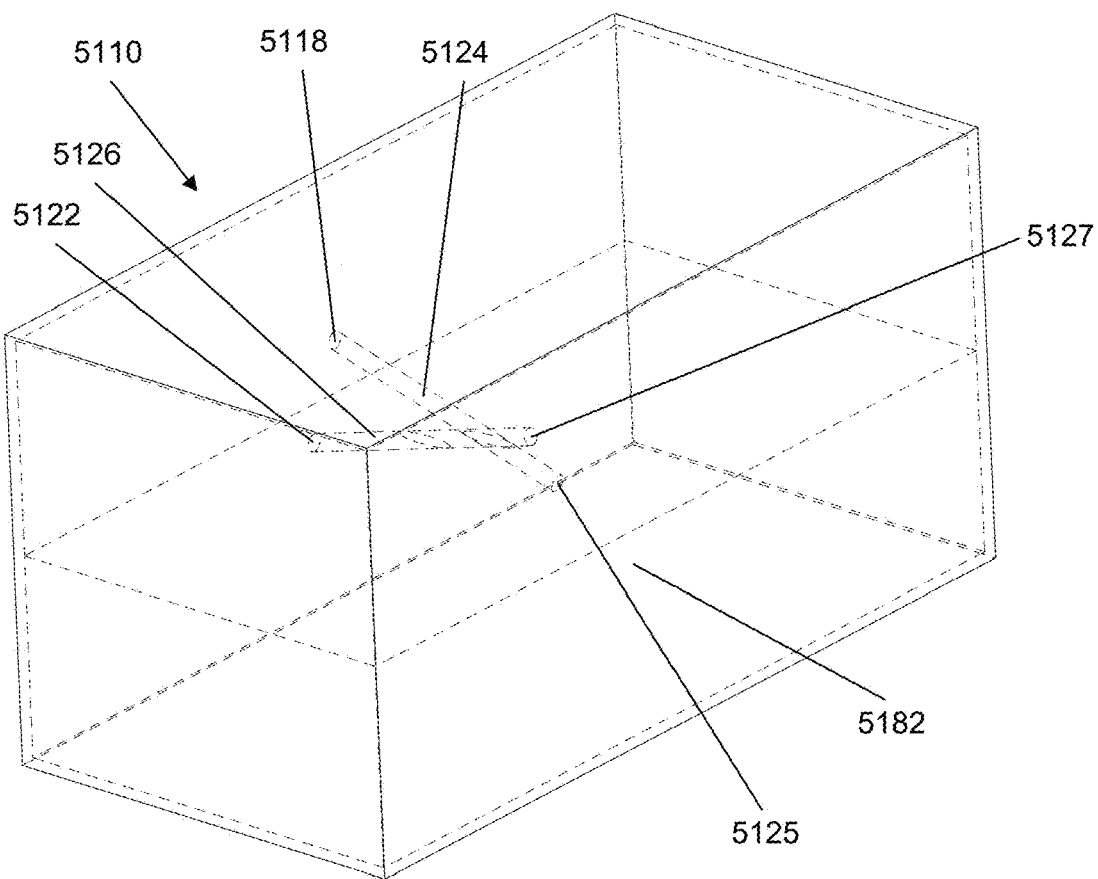
Figure 36:
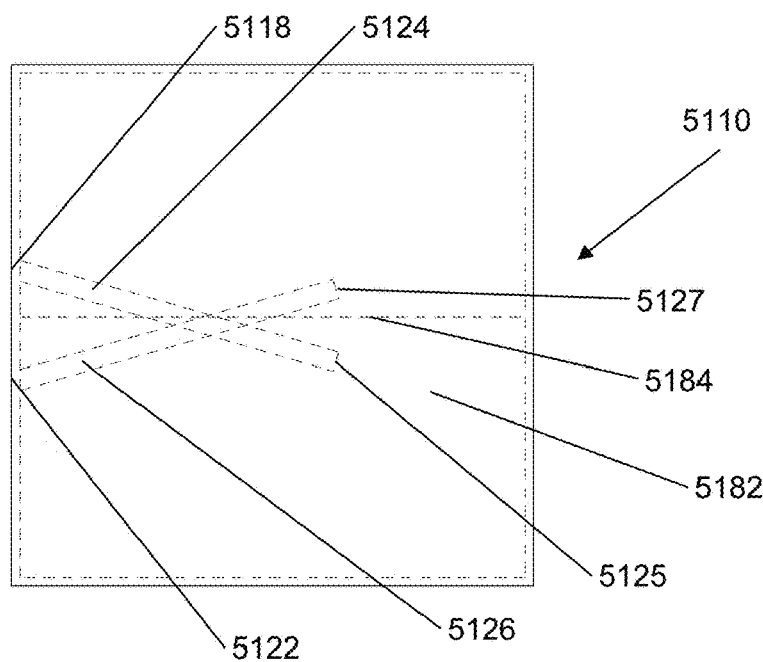
Figure 37:
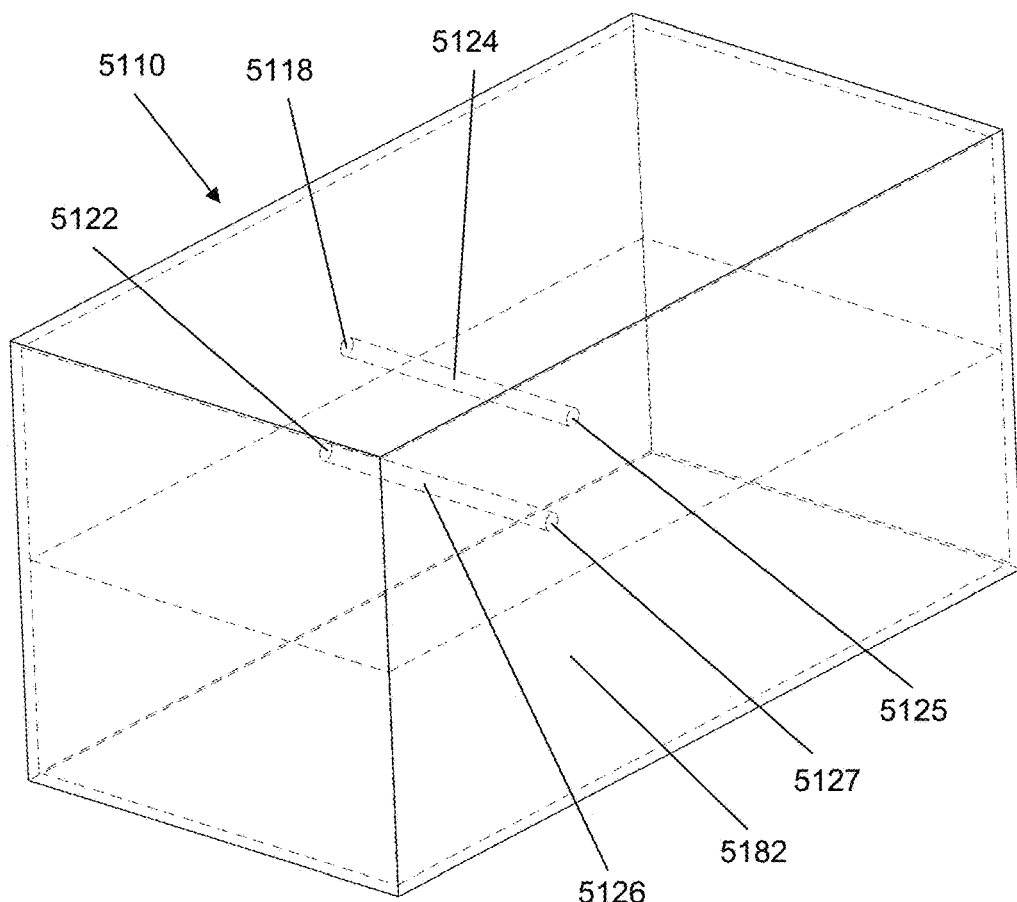
Figure 38:
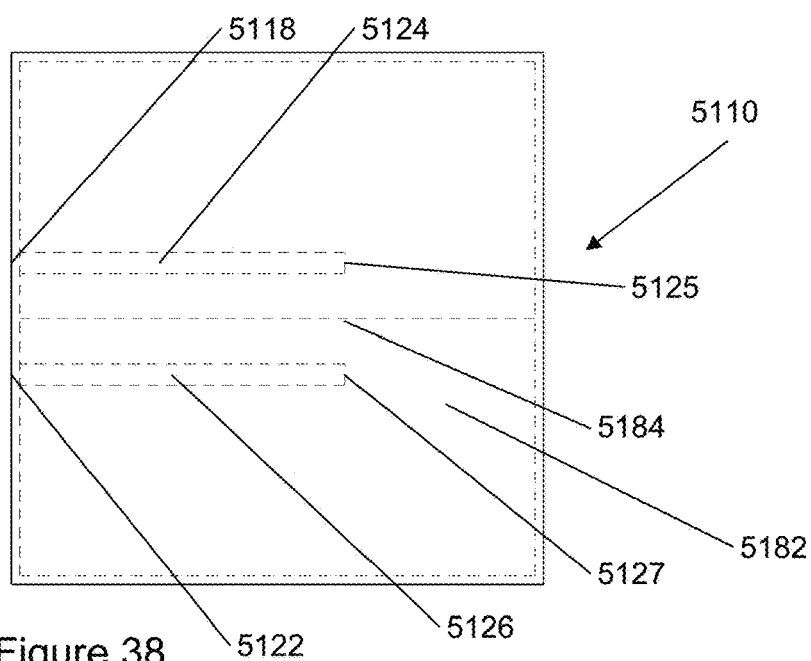

Simplified representations of the effects created by crossed inlet and outlet tubing are shown in FIG. 35-38 (FIG. 35-36 shows one configuration, FIG. 37-38 another), wherein the internal surfaces are shown by dotted lines. These figures show alternate arrangements of a water reservoir 5110, with an inlet 5118 and an outlet 5122 that respectively include an inlet tube 5124 and an outlet tube 5126 extending into a cavity or interior volume of the reservoir, and terminating at an interior end 5125 of the inlet tube 5124 and an interior end 5127 of the outlet tube 5126 respectively. FIG. 35-36 show a configuration wherein the axes of the tubing substantially intersect when viewed from the side (as shown in FIG. 36), and FIG. 37-38 show an alternate configuration wherein the axes of the tubing are substantially parallel when viewed from the side (as shown in FIG. 38). In FIG. 35-38, a volume of water 5182 is assumed to fill approximately half of the volume of the reservoir 5110, and is indicated by the dotted lines extending horizontally approximately at the mid-height of the reservoir 5110.

When the water reservoir 5110 is oriented as shown in FIG. 35-36, the arrangement of the inlet tube 5124 and the outlet tube 5126 requires the water level 5184 to rise above the entire length of the inlet tube 5124 to reach the exterior end of the inlet tube or to rise above the interior end 5127 of the outlet tube 5126 if any water 5182 is to exit the water reservoir 5110. On the other hand, in the arrangement shown in FIG. 36-37 the water level 5184 only needs to rise as high as the lower of the inlet tube 5124 or the outlet tube 5126 in order to exit the water reservoir 5110. As the water level 5184 will change as a function of the orientation of the water reservoir 5110, this effect of crossing the inlet tube 5124 and the outlet tube 5126 may be re-created at any orientation as required by re-orienting the inlet tube 5124 and the outlet tube 5126 to suit the shape of the water reservoir 5110.

The inlet tube may deliver a supply of breathable gas into the cavity of the reservoir and the outlet tube may deliver a humidified supply of breathable gas from the cavity. The inlet interior end and the outlet interior end are located within the cavity and the inlet exterior end and the outlet exterior end are located in one of the plurality of walls of the cavity. A first axis is defined by the inlet interior end and the inlet exterior end and a second axis is defined by the outlet interior end and the outlet exterior end When the reservoir is tilted approximately 90° to normal working orientation the first axis is on a first angle such that the inlet interior end and the inlet exterior end are positioned at different heights, such that the predetermined maximum volume of water is below at least one of the inlet interior end or the inlet exterior end to prevent spillback of water through the inlet tube. Furthermore, when the reservoir is tilted approximately 90° to normal working orientation the second axis is on a second angle such that the outlet interior end and the outlet exterior end are positioned at different heights, such that the predetermined maximum volume of water is below at least one of the outlet interior end or the outlet exterior end to prevent spillback of water through the outlet tube.

Overfill Prevention

Another aspect of this technology is the inclusion of an overfill protection element configured to prevent filling the reservoir above the maximum volume of water when filling the humidifier reservoir in its open configuration. In one arrangement as seen in FIGS. 30a and 30b, the overfill protection element may include at least one orifice 5138 in the water reservoir 5110 to indicate over-filling. According to this aspect of the technology, when the water reservoir 5110 is being re-filled with the reservoir lid 5114 open, over-filling beyond a predetermined level or the maximum capacity or volume for the reservoir 5110 would cause water to spill out from the orifice 5138. The water spilling out through orifice 5138 indicating that a maximum capacity has been reached and preventing the water reservoir 5110 from being filled beyond a predetermined level or maximum capacity. Advantageously water would spill out only through the at least one orifice 5138 rather than from all areas of the water reservoir resulting in less overflow spillage for the user to clean up. Thus, the at least one orifice defines an egress path of water when the predetermined maximum volume of water is exceeded. FIG. 30a show the water reservoir 5110 in its open configuration, wherein an upper flange of the base 5112 does not span the perimeter of the entire opening, creating an orifice 5138. FIG. 30b shows a zoomed in section of the base 5112 indicating the at least one orifice 5138. The at least one orifice 5138 may be in the form of one or more apertures, holes, slits or slots, or any other form that allows communication of fluid into and out of the water reservoir 5110. The at least one orifice 5138 may be formed in one or more positions around the upper flange of the base 5112.

In an alternate arrangement, the overfill protection element may include a sloped profile 5139. As shown in FIGS. 30c and 30d, the reservoir base 5112 may be arranged so that its side profile has a sloped profile 5139 in one or more directions. This arrangement may also indicate over-filling when the reservoir base 5112 is re-filled with liquid or water. In this arrangement, when the reservoir lid 5114 is in its open configuration, water may spill out at the base of the sloped profile 5139 rather than from all areas of the reservoir. Thus, the sloped profile defines an egress path of water when the predetermined maximum volume of water is exceeded. Advantages of the above methods may be that over-filling may become more difficult than has been in the prior art, and presents another advantage that in response to attempted over-filling, spillage may occur at more predictable locations.

Another aspect of this technology is that when the water reservoir 5110 is in its closed position, a seal 5192 sealingly engages the base 5112 and the reservoir lid 5114 and blocks or seals the orifice 5138 or sloped profile 5139 preventing fluid communication into and out of the water reservoir 5110. One arrangement of this feature is shown in FIG. 31, which shows that when the reservoir lid 5114 is closed (lid not shown in this image), the seal 5192 sealingly engages with the base 5112 on the outside of the orifice 5138 and no longer allows communication of liquid or air into and out of the water reservoir 5110 through the orifice 5138. Similarly the seal 5192 would engage with the base 5112 to surround the edges of the sloped profile preventing communication of liquid or air into and out of the water reservoir 5110 through the sloped profile 5139. In some arrangements the seal 5192 may be integrated with the variable portion 5116 as described above. Alternatively the seal 5192 may be a separate seal that may be used in a reservoir with or without a variable portion.

Retaining Clip

The reservoir lid 5114 may include a means by which the water reservoir 5110 is to be retained in the water reservoir dock 5130 once the two members are engaged with each other. In one arrangement a retaining means may be a protrusion, or a clip, 5142 on the reservoir lid 5114 as shown in FIGS. 32-33. FIGS. 32-33 show a water reservoir 5110 and the reservoir dock 5130. Here, a protrusion, or a clip, 5142 on the reservoir lid 5114 removably engages with a corresponding dock locking recess 5144 in the water reservoir dock 5130 when the water reservoir 5110 is inserted into the water reservoir dock 5130. This connection secures the water reservoir 5110 relative to the water reservoir dock 5130. As described above the variable portion 5116 of the reservoir is compressed to enable insertion of the reservoir into the dock 5130. The compression of the variable portion 5116 allows a portion of the reservoir 5110 to slide into the dock 5130 and allows the protrusion or clip 5142 to slide initially under the outer edge surface of the dock 5130 to reach the dock locking recess 5144. The compression force applied to the reservoir for insertion may then be released to allow the protrusion or clip 5142 to engage with the dock locking recess 5144 and securing of the reservoir 5110 within the dock 5130. When the reservoir 5110 is secured within the dock 5130 the variable portion 5116 is no longer in or in a reduced compressed state. Similarly, in order to be able to remove the water reservoir 5110 from the water reservoir dock 5130, the variable portion 5116 must be compressed as to disengage the lid protrusion 5142 from the dock locking recess 5144. It would be clear to those skilled in the art that in an alternative arrangement the lid protrusion 5142 may be a recess, and the dock locking recess 5144 may be a corresponding protrusion. Alternatively one of any number of retaining means that are known in the art may be used to achieve the same means.

5.5.2.3 Heater Plate 5120

A heater plate 5120 is used to transfer heat to the water reservoir 5110. The heater plate 5120 may form a part of the reservoir dock 5130, and may be located on or near the base of the humidifier 5000 as shown in FIG. 14. The heater plate 5120 may be formed, for example, of a nickel chrome alloy or anodised aluminium.

5.6 Glossary

In certain forms of the present technology, one or more of the following definitions may apply. In other forms of the present technology, alternative definitions may apply.

5.6.1 General

Air: Air will be taken to include breathable gases, for example air with supplemental oxygen.

Continuous Positive Airway Pressure (CPAP): CPAP treatment will be taken to mean the application of a supply of air or breathable gas to the entrance to the airways at a pressure that is continuously positive with respect to atmosphere, and preferably approximately constant through a respiratory cycle of a patient. In some forms, the pressure at the entrance to the airways will vary by a few centimeters of water within a single respiratory cycle, for example being higher during inhalation and lower during exhalation. In some forms, the pressure at the entrance to the airways will be slightly higher during exhalation, and slightly lower during inhalation. In some forms, the pressure will vary between different respiratory cycles of the patient, for example being increased in response to detection of indications of partial upper airway obstruction, and decreased in the absence of indications of partial upper airway obstruction.

5.6.2 Humidification System

Water reservoir: A water reservoir, or water tub, or humidifier reservoir, is a chamber that forms a part of the humidification system. It is configured to contain a body of liquid (e.g., water) aimed at imparting additional humidity to the flow of breathable air that passes through the water reservoir. It may comprise an air inlet and an air outlet, as well as a means (such as an opening or an openable lid) of filling the water reservoir with water.

5.6.3 Anatomy of the Respiratory System

Diaphragm: A sheet of muscle that extends across the bottom of the rib cage. The diaphragm separates the thoracic cavity, containing the heart, lungs and ribs, from the abdominal cavity. As the diaphragm contracts the volume of the thoracic cavity increases and air is drawn into the lungs.

Larynx: The larynx, or voice box houses the vocal folds and connects the inferior part of the pharynx (hypopharynx) with the trachea.

Lungs: The organs of respiration in humans. The conducting zone of the lungs contains the trachea, the bronchi, the bronchioles, and the terminal bronchioles. The respiratory zone contains the respiratory bronchioles, the alveolar ducts, and the alveoli.

Nasal cavity: The nasal cavity (or nasal fossa) is a large air filled space above and behind the nose in the middle of the face. The nasal cavity is divided in two by a vertical fin called the nasal septum. On the sides of the nasal cavity are three horizontal outgrowths called nasal conchae (singular "concha") or turbinates. To the front of the nasal cavity is the nose, while the back blends, via the choanae, into the nasopharynx.

Pharynx: The part of the throat situated immediately inferior to (below) the nasal cavity, and superior to the oesophagus and larynx. The pharynx is conventionally divided into three sections: the nasopharynx (epipharynx) (the nasal part of the pharynx), the oropharynx (mesopharynx) (the oral part of the pharynx), and the laryngopharynx (hypopharynx).

5.6.4 Materials

Silicone or Silicone Elastomer: A synthetic rubber. In this specification, a reference to silicone is a reference to liquid silicone rubber (LSR) or a compression moulded silicone rubber (CMSR). One form of commercially available LSR is SILASTIC (included in the range of products sold under this trademark), manufactured by Dow Corning. Another manufacturer of LSR is Wacker. Unless otherwise specified to the contrary, a preferred form of LSR has a Shore A (or Type A) indentation hardness in the range of about 35 to about 45 as measured using ASTM D2240.

Polycarbonate: a typically transparent thermoplastic polymer of Bisphenol-A Carbonate.

5.7 Other Remarks

Unless the context clearly dictates otherwise and where a range of values is provided, it is understood that each intervening value, to the tenth of the unit of the lower limit, between the upper and lower limit of that range, and any other stated or intervening value in that stated range is encompassed within the technology. The upper and lower limits of these intervening ranges, which may be independently included in the intervening ranges, are also encompassed within the technology, subject to any specifically excluded limit in the stated range. Where the stated range includes one or both of the limits, ranges excluding either or both of those included limits are also included in the technology.

Furthermore, where a value or values are stated herein as being implemented as part of the technology, it is understood that such values may be approximated, unless otherwise stated, and such values may be utilized to any suitable significant digit to the extent that a practical technical implementation may permit or require it.

Unless defined otherwise, all technical and scientific terms used herein have the same meaning as commonly understood by one of ordinary skill in the art to which this technology belongs. Although any methods and materials similar or equivalent to those described herein can also be used in the practice or testing of the present technology, a limited number of the exemplary methods and materials are described herein.

When a particular material is identified as being preferably used to construct a component, obvious alternative materials with similar properties may be used as a substitute.

It must be noted that as used herein and in the appended claims, the singular forms "a", "an", and "the" include their plural equivalents, unless the context clearly dictates otherwise.

All publications mentioned herein are incorporated by reference to disclose and describe the methods and/or materials which are the subject of those publications. The publications discussed herein are provided solely for their disclosure prior to the filing date of the present application. Nothing herein is to be construed as an admission that the present technology is not entitled to antedate such publication by virtue of prior invention. Further, the dates of publication provided may be different from the actual publication dates, which may need to be independently confirmed.

Moreover, in interpreting the disclosure, all terms should be interpreted in the broadest reasonable manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced.

The subject headings used in the detailed description are included only for the ease of reference of the reader and should not be used to limit the subject matter found throughout the disclosure or the claims. The subject headings should not be used in construing the scope of the claims or the claim limitations.

Although the technology herein has been described with reference to particular embodiments, it is to be understood that these embodiments are merely illustrative of the principles and applications of the technology. In some instances, the terminology and symbols may imply specific details that are not required to practice the technology. For example, although the terms "first" and "second" may be used, unless otherwise specified, they are not intended to indicate any order but may be utilised to distinguish between distinct elements. Furthermore, although process steps in the methodologies may be described or illustrated in an order, such an ordering is not required. Those skilled in the art will recognize that such ordering may be modified and/or aspects thereof may be conducted concurrently or even synchronously.

It is therefore to be understood that numerous modifications may be made to the illustrative embodiments and that other arrangements may be devised without departing from the spirit and scope of the technology.

6 REFERENCE SIGNS LIST

7 CITATIONS 7.1 Patent Literature
7.2 Non-Patent Literature

The invention claimed is:

1. A respiratory pressure treatment device for a patient, the respiratory pressure treatment device comprising:
   a pressure generator configured to supply a flow of air at positive pressure air;
   a humidifier apparatus configured to humidify the flow of air for delivery to the patient, the humidifier apparatus being integrated in the respiratory pressure treatment device, the humidifier apparatus comprising:
      a dock comprising a spring-biased heater plate and a recess; and
      a water reservoir configured to be engaged with the dock and comprising a chamber that is, when the water reservoir is in an operative position with the dock, in fluid communication with the flow of air, the water reservoir further comprising:
         a base structured to hold a volume of water and including a conductive portion in thermal engagement with the heater plate when the water reservoir is received on the dock;
         a lid movably connected to the base between a closed position and an open position, the lid including an upper surface that is exposed when the water reservoir is secured in the operative position and in sealed fluid communication with the dock;
         a seal that seals between the base and the lid when the lid is in the closed position; and
         a protrusion configured to be locked within the recess to secure the reservoir to the dock in the operative position, the protrusion including an exterior portion extending outward from an exterior surface of the water reservoir when the base and the lid are in the closed position, the protrusion being spaced from and distinct from the upper surface that is exposed when the water reservoir is secured in the operative position, the protrusion not being exposed when the water reservoir is secured in the operative position and in sealed fluid communication with the dock; and
      a resilient portion configured to be compressed upon direct application of a downwards force to the upper surface of the water reservoir lid that is exposed whilst the water reservoir is secured in the operative position and in sealed fluid communication with the dock to unlock the protrusion from within the recess and thus enable removal of the reservoir from the dock.

2. The respiratory pressure treatment device according to claim 1, wherein the water reservoir further comprises an inlet to receive the flow of air and an outlet to deliver the flow of air with added humidity back to an outlet of the dock.

3. The respiratory pressure treatment device according to claim 2, wherein the lid comprises the inlet and the outlet.

4. The respiratory pressure treatment device according to claim 2, wherein the inlet and the outlet are located on a common side of the water reservoir and configured to guide the flow of air in a substantially horizontal direction to and from the dock when the humidifier apparatus is in the operative position.

5. The respiratory pressure treatment device according to claim 4, wherein the inlet and the outlet are located at different vertical heights relative to the conductive portion.

6. The respiratory pressure treatment device according to claim 2, wherein the inlet comprises an inlet tube and the outlet comprises an outlet tube.

7. The respiratory pressure treatment device according to claim 6, wherein an axis of the inlet tube and an axis of the outlet tube are crossed relative to one another.

8. The respiratory pressure treatment device according to claim 6, wherein an axis of the inlet tube and an axis of the outlet tube are angled relative to the conductive portion of the base.

9. The respiratory pressure treatment device according to claim 2, wherein the dock comprises a dock air outlet to deliver the flow of air to the inlet of the water reservoir and a dock air inlet to receive the flow of air that has been humidified in the reservoir.

10. The respiratory pressure treatment device according to claim 1, wherein the water reservoir further includes a latch to secure the base and the lid together.

11. The respiratory pressure treatment device according to claim 10, wherein the latch is configured to restrict relative movement of the lid and the base in one direction only to prevent separation of the lid and the base while allowing further compression of the resilient portion.

12. The respiratory pressure treatment device according to claim 1, wherein the water reservoir is structured to prevent refilling of the reservoir when the reservoir is coupled to the dock.

13. The respiratory pressure treatment device according to claim 1, wherein at least a portion of the water reservoir is prevented from being opened when the reservoir is coupled to the dock.

14. The respiratory pressure treatment device according to claim 1, wherein the dock further comprises a cavity having a top portion and a bottom portion, the bottom portion having the heater plate located thereon and the top portion having the recess, the cavity configured to retain at least a portion of the water reservoir therein.

15. The respiratory pressure treatment device according to claim 1, wherein the base and the lid are pivotably coupled.

16. The respiratory pressure treatment device according to claim 1, wherein the resilient portion is located within a wall of the lid.

17. The respiratory pressure treatment device according to claim 1, wherein the water reservoir further comprises at least one handle to facilitate coupling of the reservoir to the dock.

18. The respiratory pressure treatment device according to claim 1,
   wherein the water reservoir further comprises an inlet to receive the flow of air and an outlet to deliver the flow of air with added humidity back to an outlet of the dock, wherein the inlet and the outlet are located on a common side of the water reservoir and contained in a common planar side wall when the humidifier apparatus is in the operative position, the inlet and outlet being configured to guide the flow of air in a substantially horizontal direction to and from the dock when the humidifier apparatus is in the operative position, wherein the inlet and the outlet are located at different vertical heights relative to the conductive portion, wherein the inlet comprises an inlet tube and the outlet comprises an outlet tube, wherein the dock comprises a dock air outlet to deliver the flow of air to the inlet of the reservoir and a dock air inlet to receive the flow of air that has been humidified in the reservoir, wherein the reservoir further includes a latch to secure the base and the lid together, wherein the reservoir is structured to prevent refilling of the reservoir when the reservoir is coupled to the dock, wherein at least a portion of the reservoir is prevented from being opened when the reservoir is coupled to the dock, wherein the dock further comprises a top portion and a bottom portion, the bottom portion having the heater plate located thereon and the top portion having the recess, the dock including a cavity configured to retain at least an insertion end of the reservoir therein, wherein the lid is configured to swing open relative to the base about an axis located at the insertion end of the reservoir, wherein the lid is configured to pivot in order to release the protrusion from the recess upon application of the downwards force to the upper surface of the water reservoir lid, wherein the resilient portion is located within a wall of the lid, wherein the seal is anchored to the base and includes a base portion and a cantilevered lip that extends from the base portion, wherein the resilient portion does not form a seal between the lid and the base, wherein the reservoir comprises at least one handle configured to facilitate horizontal sliding of the reservoir out of engagement with the dock whilst compressing the resilient portion; and wherein the water reservoir is simultaneously sealed and secured to the dock upon reaching the operative position in which the water reservoir is slid into the dock to a maximum extent.

19. The respiratory pressure treatment device according to claim 1, wherein the lid further comprises an inlet to receive the flow of air and an outlet to deliver the flow of air with added humidity back to an outlet of the dock, wherein the inlet and the outlet are located on a common planar wall of the lid and configured to guide the flow of air in a substantially horizontal direction to and from the dock when the humidifier apparatus is in the operative position, wherein the inlet comprises an inlet conduit and the outlet comprises an outlet conduit, wherein an axis of a portion of the inlet conduit and an axis of a portion of the outlet conduit are crossed relative to one another, wherein the dock comprises a dock air outlet to deliver the flow of air to the inlet of the reservoir and a dock air inlet to receive the flow of air that has been humidified in the reservoir, wherein the reservoir further includes a latch to secure the base and the lid together, wherein the seal has a base portion anchored to the lid and a cantilevered lip that extends from the base portion, wherein the resilient portion does not form a seal between the lid and the base, wherein the resilient portion is independent of the lid and the base, wherein the base and the lid are pivotably coupled together; and wherein the water reservoir is simultaneously sealed and secured to the dock upon reaching the operative position in which the water reservoir is engaged with the dock to a maximum extent.

20. The respiratory pressure treatment device according to claim 1, wherein the resilient portion is independent of the lid and the base.

21. The respiratory pressure treatment device according to claim 1, wherein the water reservoir is simultaneously sealed and secured to the dock upon reaching the operative position in which the water reservoir and the dock are fully assembled.

* * * * *